(12) United States Patent
Dahlbäck

(10) Patent No.: US 7,169,572 B1
(45) Date of Patent: Jan. 30, 2007

(54) ASSAYS FOR DETERMINING ANTICOAGULANT COFACTOR ACTIVITY

(75) Inventor: Björn Dahlbäck, Malmö (SE)

(73) Assignee: T.A.C. Thrombosis and Coagulation AB, Malmo (SE)

( * ) Notice: Subject to any disclaimer, the term of this patent is extended or adjusted under 35 U.S.C. 154(b) by 1147 days.

(21) Appl. No.: 08/500,917

(22) PCT Filed: Jan. 28, 1994

(86) PCT No.: PCT/SE94/00070

§ 371 (c)(1),
(2), (4) Date: Oct. 20, 1995

(87) PCT Pub. No.: WO94/17415

PCT Pub. Date: Aug. 4, 1994

(30) Foreign Application Priority Data

| Jan. 29, 1993 | (SE) | ................................. 9300300 |
| Jul. 20, 1993 | (SE) | ................................. 9302457 |

(51) Int. Cl.
C12Q 1/56 (2006.01)
G01N 33/573 (2006.01)
G01N 33/86 (2006.01)

(52) U.S. Cl. ............................ 435/7.4; 435/13; 436/69
(58) Field of Classification Search ................... 435/6, 435/7.4, 13; 436/69
See application file for complete search history.

(56) References Cited

U.S. PATENT DOCUMENTS

| 4,622,389 | A |   | 11/1986 | Nagasawa et al. |
| 4,692,406 | A |   | 9/1987 | Becker et al. |
| 4,849,403 | A |   | 7/1989 | Stocker et al. |
| 5,001,069 | A |   | 3/1991 | Bartl et al. |
| 5,051,357 | A |   | 9/1991 | Hassouna |
| 5,059,525 | A |   | 10/1991 | Bartl et al. |
| 5,147,805 | A | * | 9/1992 | Preda et al. .................. 436/69 |
| 5,169,786 | A |   | 12/1992 | Carroll et al. |
| 5,200,322 | A | * | 4/1993 | Matsumoto ................... 435/13 |
| 5,308,756 | A | * | 5/1994 | van de Waart et al. ....... 435/13 |
| 5,314,695 | A |   | 5/1994 | Brown |
| 5,439,802 | A |   | 8/1995 | Rosén |
| 5,443,960 | A |   | 8/1995 | Dählback |
| 5,472,850 | A |   | 12/1995 | Morrissey |
| 5,506,112 | A |   | 4/1996 | Lang et al. |
| 5,525,478 | A | * | 6/1996 | Matschiner ................... 435/13 |
| 5,643,739 | A | * | 7/1997 | Varadi et al. .................. 435/13 |
| 5,716,795 | A | * | 2/1998 | Matschiner ................... 435/13 |
| 5,780,255 | A | * | 7/1998 | Preda ............................ 435/23 |
| 5,834,223 | A | * | 11/1998 | Griffin et al. .................. 435/13 |
| 6,083,757 | A | * | 7/2000 | Griffin et al. .................. 436/69 |
| 2003/0143759 | A1 |   | 7/2003 | Dahlbäck |

FOREIGN PATENT DOCUMENTS

| EP | A 0 229 234 | 7/1987 |
| EP | 0286323 | 10/1988 |
| EP | 0434377 | 6/1991 |
| WO | 90 11368 | 10/1990 |
| WO | 91 01382 | 2/1991 |
| WO | 91 01383 | 2/1991 |
| WO | 91 02812 | 3/1991 |
| WO | WO 92/08479 | 5/1992 |
| WO | WO 93/10261 | 5/1993 |

OTHER PUBLICATIONS

Wolf et al, Thrombosis and Haemostasis, 62, 1144-1145, 1989.*
Dahlbäck et al., "Resistance to activated protein C, the FV:Q$^{506}$ allele, and venous thrombosis" *Ann. Hematol.* 72:166-176 (1996).
Dahlbäck, "New Molecular Insights Into the Genetics of Thrombophilia. Resistance to Activated Protein C Caused by Arg$^{506}$ to Gln Mutation in Factor V as a Pathogenic Risk Factor for Venous Thrombosis" *Thromb. Haemost.* 74(1):139-148 (1995).
Dahlbäck, "Factor V gene mutation causing inherited resistance to activated protein C as a basis for venous thromboembolism" *J. Intern. Med.* 237:221-227 (1995).

(Continued)

*Primary Examiner*—David Saunders
(74) *Attorney, Agent, or Firm*—Kirkpatrick & Lockhart Nicholson Graham LLP

(57) ABSTRACT

Methods are disclosed for determining, in a sample derived from a human, the functional activity of a component of the human blood coagulation system, which activity can be correlated to conversion of a substrate specific for activated Protein C (APC), by measuring in an assay medium containing the sample and a substrate for APC, the conversion of the substrate by APC and correlating the conversion to the functional activity of the component. When the component is anticoagulant Factor V, at least one of exogenous APC, Protein S or an inhibitor of Protein S activity is added to the medium. When the component is Protein C, APC, or Protein S, exogenous anticoagulant Factor V or an inhibitor of anticoagulant activity of Factor V is added to the medium. Methods are also disclosed for diagnosing a blood coagulation/anticoagulation disorder or for determining a predisposition thereto in a human by determining anticoagulant Factor V activity in an assay medium containing a sample derived from the human.

23 Claims, 5 Drawing Sheets

OTHER PUBLICATIONS

Bertina et al., "Mutation in blood coagulation factor V associated with resistance to activated protein C" *Nature* 369:64-47 (1994).

Dahlbäck, et al., "Inherited resistance to activated protein C is corrected by anticoagulant cofactor activity found to be a property of factor V", *Proc. Natl. Acad. Sci. (USA)* 91:1396-1400 (1994).

Zoller et al., "Linkage between inherited resistance to activated protein C and factor V gene mutation in venous thrombosis", *The Lancet* 343:1536-1538 (1994).

Chromogenix, Coatest APC Resistance Kit instructions, May 1993.

Chromogenix, Coatest APC Resistance Kit Brochure, Jun. 1993.

Tuddenham, E.G.D., "Thrombophilia: a new factor emerges from the mists", *The Lancet*, 342:1501-1506 (Dec. 1993).

Kalafatis, M., et al., "Role of the Membrane in the Inactivation of Factor Va by Activated Protein C", *J. Biol. Chem.* 268:27246-27257 (1993).

Walker and Fay, "Regulation of Blood Coagulation by the Protein C System", *FASEB J.* 6:2561-2567 (1992).

Esmon, C.T., "The Roles of Protein C and Thrombomodulin in the Regulation of Blood Coagulation", *J. Biol. Chem.* 264:4743-4746 (1289).

Pratt, C.W., et al., "Protein C Inhibitor: Purification and Proteinase Reactivity", *Thrombos. Res.* 53:595-602 (1989).

Dahlbäck, B., "A New Model for Coagulation Factor V Suggesting a Unique Mechanism of Activation", *Scand. J. Clin. Lab. Invest.*, 48, Suppl. 191:47-61 (1988).

Kane and Davie, "Blood Coagulation Factors V and VII: Structural and Functional Similarities and Their Relationship to Hemorrhagic and Thrombotic Disorders", *Blood* 71(3):539-555 (1988).

Solymoss, et al., "Kinetics of Inactivation of Membrane-bound Factor Va by Activated Protein C. Protein S Modulates Factor Xa Protection", *J. Biol. Chem.* 263:14884-14890 (1988).

Esmon, C.T., "The Regulation of Natural Anticoagulant Pathways", *Science* 235:1348-1352 (1987).

Miletich, et al., "Absence of Thrombosis in Subjects with Heterozygous Protein C Deficiency", *New Eng. J. Med.* 317:991-996 (1987).

Walker, et al., "Inactivation of Factor VIII by Activated Protein C and Protein S", *Arch. Biochem. Biophys.* 252:322-328 (1987).

Giddings, J.C., et al. "Chapter 12: Laboratory Support in the Diagnosis of Coagulation Disorders" *Clinics in Haematology*, 14(2):571-596 (1985).

Root-Bernstein and Westall, "Fibrinopeptide A Binds Gly-Pro-Arg-Pro", *Proc. Natl. Acad. Sci. (USA)* 81:4339-4342 (1984).

Stenflo, "Structure and Function of Protein C", *Semin. Thromb. Haemost.* 10:109-121 (1984).

Walker, F., "Protein S and the Regulation of Activated Protein C", *Semin. Thromb. Haemost.* 10:131-138 (1984).

Esmon, C.T., "Protein C: Biochemistry, Physiology and Clinical Implications", *Blood*, 62:1155-1158 (1983).

Laudano, et al., "Synthetic Peptides Modeled on Fibrin Polymerization Sites", *Ann NY Acad. Sci.* 408:315-329 (1983).

Salem, et al., "Human Coagulation Factor Va is a Cofactor for the Activation of Protein C", *Proc. Nat. Acad. Sci. USA* 80:1584-1588 (1983).

Suzuki, et al., "Inactivation of Human Coagulation Factor V by Activated Protein C", 258:1914-1920 (1983).

Walker, "Regulation of Bovine Activated Procein C By Proten S: The Role of the Cofactor Protein In Species Specificity", *Thromb. Res.* 22:321-327 (1981).

Laudano and Doolittle, "Studies on Synthetic Peptides that Bind to Fibrinogen and Prevent Fibrin Polymerization. Structural Requirements, Number of Binding Sites, and Species Differences", *Biochemistry* 19:1013-1019 (1980).

Walker, J., "Regulation of Activated Protein C by a New Protein", *Biol. Chem.* 255:5521-5524 (1980).

Kisiel, W., "Human Plasma Protein C: Isolation, Characterization and Mechanism of Activation by Alpha Thrombin", *J. Clin. Invest* 64:761-769 (1979).

Walker, et al., "The Inhibition of Blood Coagulation by Activated Protein C Through the Selective Inactivation of Activated Factor V", *Biochem. Biophys. Acta* 571:333-342 (1979).

Laudano and Doolittle, "Synthetic Peptide Derivatives that Bind to Fibrinogen and Prevent the Polymerization of Fibrin Monomers", *Proc. Natl. Acad. Sci. (USA)* 75:3085-3089 (1978).

DiScipio, et al., "A Comparison of Human Prothrombin, Factor IX (Christmas Factor), Factor X (Stewart Factor) and Protein S", *Biochem.* 16:698-704 (1977).

Kisiel, et al., "Anticoagulant Properties of Bovine Plasma Protein C Following Activation By Thrombin", *Biochem* 16:5824-5831 (1977).

Kisiel, et al., "Proteolytic activation of Protein C from Bovine Plasma", *Biochem.* 15:4893-4900 (1976).

Seegers, et al., "Relationship of 'New' Vitamin K-Dependent Protein C and 'Old' Autoprothrombin II-A", *Thromb. Res* 8:543-552 (1976).

Marciniak, "Coagulation Inhibitor Elicited by Thrombin", *Science* 170:452-453 (1970).

Beck et al. (1988), "Protein C: ein Inhibitor der Blutgerinnung," *Diagnose & Labor*, 38:35-42 (Abstract in English).

Bertina (1990), "Specificity of Protein C and Protein S Assays," *Res. Clin. Lab.*, 20:127-138.

Bertina et al. (1985) "Determination of Plasma Protein S—The Protein Cofactor of Activated Protein C," *Thrombosis Haemostasis*, 268-272.

Comp (1990), "Laboratory Evaluation of Protein S Status," *Seminars in Thromb. and Haemost.*, 16(2):177-181.

"Correlation of the APC Ratio with Free Portein S Antigen and with Protein C Activity" Appendix 5, publication date not known.

Dade Behring Marburg GmbH (2000), "Pathromitin®," 1 page (Partial English translation provided).

Diagnostika Stago "Staclot® Protein C Additional Information," 1 page, publication date unknown.

Diagnostica Stago "Staclot® Protein S Additional Information," 1 page, publication date unknown.

Edson et al. (1990), "Laboratory Diagnosis of Inherited Protein S Deficiency," *Am. J. Clin. Pathol.*, 94(2):176-186.

Exner et al. (1978), "A Sensitive Test Demonstrating Lupus Anticoagulant and its Behavioural Patterns," *Br. Haematol.*, 40:143-151.

Faioni et al. (1991), "Low Levels of the Anticoagulant Activity of Protein C in Patients with Chronic Renal Insufficiency: an Inhibitor of Protein C is Present in Uremic Plasma," *Thrombosis and Haemostasis*, 66(4):420-425.

Han et al. (1990), "A Simple Functional Protein S Assay Using PROTAC®," *Clin. Lab. Haemat.*, 12:201-208.

Hoffmann et al. (1978), "Comparison of Reagents for Determining the Activated Partial Thromboplastin Time," *Thromb. Haemost.*, 39:640-645.

Holmberg et al. (1981), "Assessment of Blood Coagulation and General Haemostatis," *Haemostasis and Thrombosis* (Bloom et al. Ed.), Churchill Livingston, London, 768-774.

Hoogendoorn et al. (1991), "$\alpha_2$-Macroglobulin Binds and Inhibits Activated Protein C," *Blood*, 78(9):2283-2290.

Koepke et al. (1986), "Partial Thromboplastin Time-Test Proposed Performance Guidelines," *Thrombosis and Haemostasis*, 55:143-144.

Koster et al. (1993) "Venous Thrombosis Due to Poor Anticoagulant Response to Activated Protein C: Laiden Thrombophilia Study," *The Lancet*, 342:1503-1506.

Lottenberg et al. (1981), "Assay of Coagulation Proteases Using Peptide Chromogenic and Fluorogenic Substrates," *Methods in Enzymology* (Colowick et al. Ed.), vol. 8, Protedytic Enzymes Past C (Lorand Ed.), Academic Press, 341-361.

Maccaferri et al. (1991), "Protein S Activity in Patients with Heredofamilial Protein S Deficiency and in Patients with Juvenile Venous Thrombosis. Results of a Functional Method," *Thromb. Res.*, 64:647-658.

Malm et al. (1988), "Changes In the Plasma Levels of Vitamin K-dependent Proteins C and S of C4b-binding Protein During Pregnancy and Oral Contraception," *Br. Hemat.*, 68:437-443.

Marlar et al. (1982), "Mechanism of Action of Human Activated Protein C, a Thrombin-Dependent Anticoagulant Enzyme," *Blood*, 59(5):1067-1072.

Pollner et al. (1992), "The Activated Partial Thromboplastin Time (APTT)," ECAT Assay Procedures-A Manual of Laboratory Techniques (Jespersen et al. Ed.), Kluwer Academic Publishers, 35-40.

Preda et al. (1990), "A Prothrombin Time-Based Functional Assay of Protein S," *Thromb. Res.*, 60:19-32.

Rosén et al. "Protein S, An Important Regulatory Protein in Hemostasis," *Protein S—Chromogenix Monograph Series*, 21 pgs, publication date unkown.

Salem et al. (1983), "Human Coagulation Factor Va is a Cofactor for the Activation of Protein C," *Proc. Nat. Acad. Sci. USA*, 80:1584-1588.

Spaethe (1984), "Hämostase-Physiologie, Pathophysiologie, Diagnostik," 90 (English translation provided).

Stocker et al. (1988), "Practical Application of the Protein C Activator Protac from *Agkistrodon contortrix* Venom," *Folia Haematol.*, 115:260-263.

Stocker et al. (1986), "Protein C Activators in Snake Venoms," *Behring Inst. Mitt.*, 37-47.

Tripodi et al. (1992), "Recombinant Tissue Factor as Substitute for Conventional Thromboplastin in the Prothrombin Time Test," *Thromb. Haemost.*, 67(1):42-45.

Vasse et al. (1989), "Protein C: Rouen, A New Hereditary Protein C Abnormality with Low Antiocoagulant but Normal Amidolytic Activites," *Thrombosis Research*, 56:387-398.

Vukovich et al. (1988), "Replacement Therapy for a Homozygous Protein C Deficiency-State Using a Concentrate of Human Protein C and S," *Br. Haemat.*, 70(4):435-440.

Walker. (1990), "Guidelines on The Investigation and Management of Thrombophilia," *J. Clin. Pathol.*, 43:703-710.

Wiesel et al. (1990), "Screening of Protein S Deficiency Using a Functional Assay in Patients with Venous and Arterial Thrombosis," *Thromb. Res.*, 58:461-468.

Wolf et al. (1991), "Functional Assay of Protein S in 70 Patients with Congenital and Acquired Disorders," *Blood Coag. Fibin.*, 2:705-712.

Woodhams et al. (1990), "Functional Protein S Assay Shows Improved Correlation with Clinical Symptoms in Hereditary Deficiency," *Thromb. Res.*, 57:651-657.

Deutsche Norm, DIN 58 911 (1988), "Kalibrierung ven Gerinnugngszeit-MeBverfahren," 3 pages (English translation provided).

Deutsche Norm DIN 58 939 (1987), "Refererzplasma," 4 pages (English translation provided).

Hypercoaguability-A New Cofactor in the Protein C Anticoagulant Pathway, Bauer, New England Journal of Medicine, 1994, vol. 330, pp. 566-567.

Fast Functional Assay of Protein C, :Takahashi, Clinica Chimica Acta 1275 (1988) 217-226.

Protein C:Roen, A New Hereditary, Vasse, . . . Thrombosis Research 56: 387-398, 1989.

Familial thrombophilia due to a previously unrecognized mechanism characterized by poor anticoagulant response to activated protein C . . . , Dählback, Proc.Natl.Acad.Sci. USA, vol. 90, 1993, pp. 1004-1008.

Replacement therapy for a homozygous protein C deficiency-state using a concentrate of human protein C anad S, Haematol, Dec. 1988, 70(4) pp. 435-440.

Isolation of functional human coagulation factor V by using a hybridoma antibody, Katzmann, Proc.Natl.Acad.Sci. USA, 1981, 78(1) pp. 162-166.

Gene Structure of human thrombomodulin, a thrombin receptor on endothelium acting as a cofactor for . . . , Nippon Ketsueki Gakki Zasshi, Dec. 1988, 51(8), pp. 1655-1664.

A Fatal Thrombotic Disorder Associated with An Acquired Inhibitor of Protein C, Mitchell et al., New England Journal of Medicine, 1987, vol. 317, 1638-42.

Impairment of the Protein C Anticoagulant Pathway in a Patient with Systemic Lupus Erythematosus, Anticardiolipin Antibodies and Thrombosis, Amer et al., Thrombosis Research 57, pp. 247-258, 1990.

Factor VIII Defect Associated with . . . Thrombosis & Haemostasis, Dählback et al., 65 Abstract 39, 658 (1991).

Anticoagulant Protein C Pathway Defective in Majority of Thrombophilic Patients, J. Griffin et al., Blood, vol. 82, No. 7, pp. 1989-1993, Oct. 1, 1993.

Resistance to Activated Protein C in Nine Thrombophilic Families:Interference in a Protein S Functional Assay, E. M. Faioni et al., Thrombosis and Haemostasis, F.K. Schattauer Verlagsgesellschaft mBH, 70(6) 1067-1071 (1993).

* cited by examiner

US 7,169,572 B1

ASSAYS FOR DETERMINING ANTICOAGULANT COFACTOR ACTIVITY

RELATED APPLICATIONS

Priority is claimed to International Application PCT/SE94/00070, filed Jan. 28, 1994, which claims priority to Swedish Application No. 9300300-2, filed Jan. 29, 1993, and Swedish Application No. 9302457-8, filed Jul. 20, 1993.

FIELD OF THE INVENTION

The present invention is related to the diagnosis and treatment of blood coagulation disorders. In particular, the present invention is generally related to a novel anticoagulant cofactor activity involved in the human blood coagulation system and possibly also involved in the blood coagulation system of some other mammalian species.

BACKGROUND OF THE INVENTION

Blood coagulation is a complex system involving a large number of proteins that function in concert with platelets to yield hemostasis. The coagulation system is strictly regulated by a series of anticoagulant proteins present in plasma and on the surface of endothelial blood cells (Esmon, J. Biol. Chem. 264 (1989) 4743–4746; Bauer, Sem. Hematol. 28 (1991)10–18; and Rapaport, Blood 73 (1989) 35965). Under physiological conditions, pro- and anti-coagulant mechanisms are delicately balanced to provide hemostasis and coagulation. Disturbances in this balance result in either bleeding or thromboembolic disorders.

The present invention is related to a novel activity involved in a physiologically important anticoagulant system associated with Protein C and Protein S that has been elucidated in recent years and is shown as part of the blood coagulation interactions illustrated in FIG. 5.

In the above mentioned anticoagulant system, Protein C, a vitamin K-dependent plasma protein, is a key component that, after activation to Activated Protein C (APC) on endothelial cells by the thrombin/thrombomodulin complex, selectively degrades the coagulation Factors Va and VIIIa, i.e., the activated forms of the coagulation Factors V and VIII, respectively. (Esmon, supra; Stenflo, in Protein C and Related Proteins, ed. Bertina (Churchill Livingstone Longham Group, UK) (1988) 21–54; Mann et al., Ann. Rev. Biochem. 57 (1988) 915–956; and Kane et al., Blood 71 (1988) 539–55).

The activity of APC is influenced by another vitamin K-dependent plasma protein, designated Protein S, which functions as a cofactor to APC in the degradation of Factors Va and VIIIa (Esmon, supra; Stenflo, supra; and Dahlbäck, Thromb. Haemostas. 66 (1991) 49–61).

The above mentioned Factors Va and VIIIa are phospholipid-bound cofactors involved in the activation of Factor X and prothrombin, respectively, and are, thus, indirectly involved in the conversion of fibrinogen to fibrin, i.e., in clot formation. Accordingly, the rate of the coagulation reaction is dependent on the balance between the activation of Factors VIII and V and the degradation of their activated forms, the unactivated Factors VIII and V being poor substrates for APC.

Disturbances in the blood coagulation system are frequently manifested as serious and often life-threatening conditions, and knowledge about the underlying causes for the disturbances is often crucial in order to enable diagnosis and/or successful therapy of a manifested disease or the screening of individuals having a predisposition for a blood coagulation disease. For instance, therapeutic use of purified Protein C has been developed as a result of the discovery of Protein C deficiency associated with thrombophilia.

Thrombophilia can be defined as a tendency towards early-onset venous thomboembolic disease in adults in the absence of known risk factors. Although abnormalities have been determined for some thrombophilic patients, in the majority of such cases no laboratory test abnormalities were identified.

The present invention is related to a new defect in anticoagulant response to activated Protein C, called APC-resistance, which has been shown to be inherited and associated with familial thrombophilia.

In a few cases thrombophilia has been associated with hypothetical factors, such as an anti-Protein C antibody (Mitchell et al., New England Journal of Medicine, 1987, Vol. 316, 1638–1642), an anti-cardiolipin antibody (Amer et al., Thrombosis Research 57 (1990) 247–258) and a defective Factor VIII molecule (Dahlbäck et al., Thromb. Haemost. 65, Abstract 39, 658 (1991)).

In WO 93/10261, in vitro methods for the diagnosis of a manifested blood coagulation disorder or for the screening of individuals predisposed to a blood coagulation disorder are disclosed. These methods are based on measurement of the anticoagulant response to exogenous APC added to a plasma sample from the individual to be tested, a weak anticoagulant response to APC, i.e., APC-resistance, indicating manifestation of or predisposition to blood coagulation disorders, and especially a thromboembolic disease. No explanation for APC-resistance is given but the resistance to APC is suggested to be due to unknown interactions in the blood coagulation system or to unknown coagulation factor(s) thereof. However, several possible explanations connecting the APC-resistance to functional Protein S deficiency, a Protein C inhibitory antibody, a protease inhibitor for APC or a mutation giving an APC-resistant Factor Va molecule or a Factor VIII gene mutation were ruled out.

DETAILED DESCRIPTION OF THE INVENTION

Figure 1:
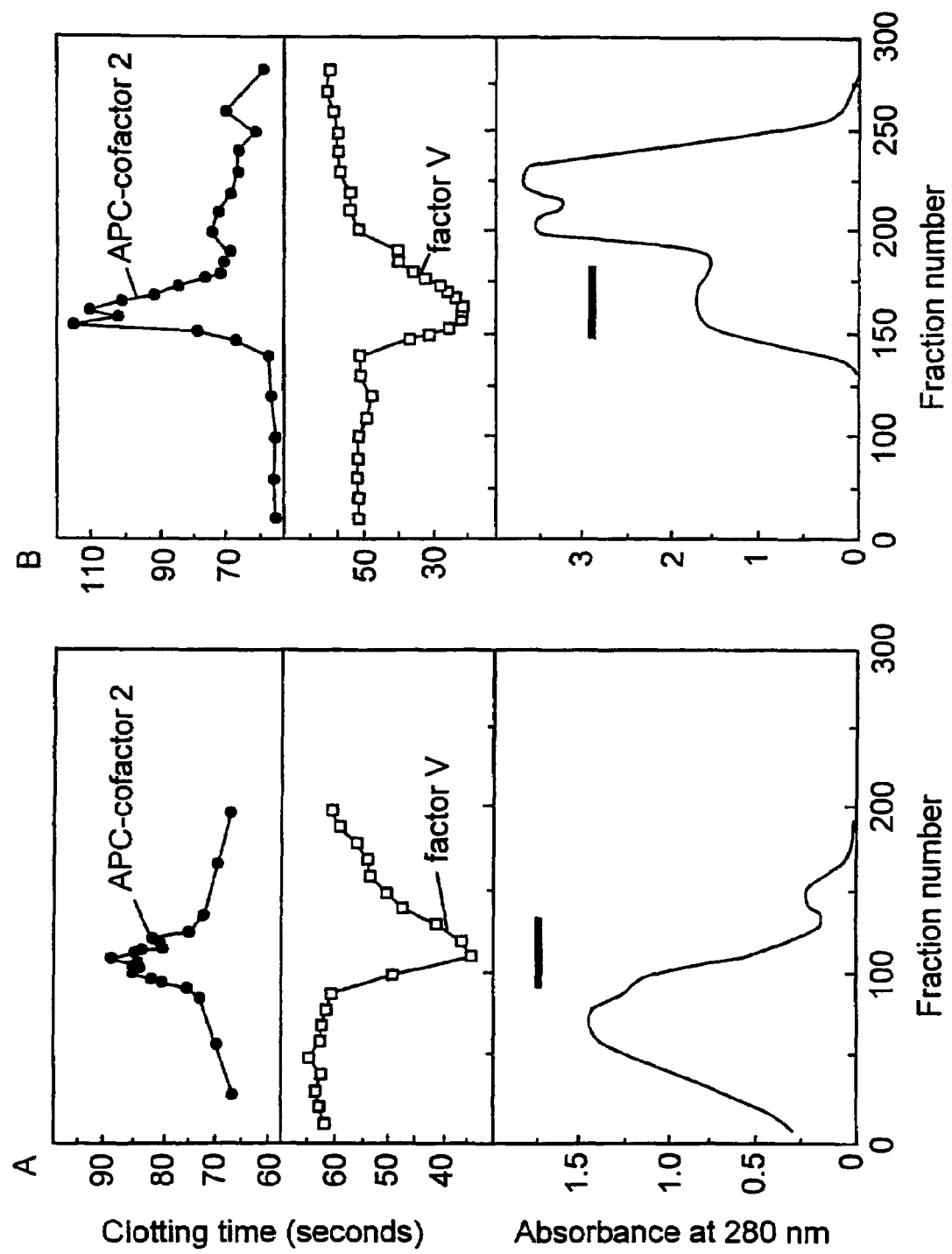
FIG. 1 illustrates chromatography on Q-Sepharose (A) and Sephacryl S-300 (B) of Factor V and APC-cofactor 2 activity.

According to the present invention it has been found that APC-resistance is due to deficiency of a previously unrecognized anticoagulant cofactor activity enhancing the proteolytic effect of APC directed against Factor Va and Factor VIIIa. The findings that form the basis for the discovery of the present anti-coagulant cofactor activity have been reported in Dahlbäck et al., Proc. Natl. Acad. Sci. USA, 90

(1993) 1004–1008, said reference having a publication date after the earliest priority date claimed for the present application.

More specifically, this anticoagulant activity has been found to be expressed by Factor V, a finding that is quite surprising, since Factor V is the precursor to the procoagulant Factor Va, the latter being degraded by APC in the above mentioned Protein C anticoagulant system. Thus, Factor V is the second cofactor that has been found for APC, the first one being Protein S as mentioned above. Accordingly, the present novel anticoagulant cofactor activity is designated "APC-cofactor 2 activity" or "Factor V anticoagulant activity" and, where appropriate, Factor V is also designated "APC-cofactor 2". The prior known activity of Factor V is designated "Factor V procoagulant activity". However, the possibility that the said activity is associated with Factor Va cannot be ruled out entirely.

The discovery of the novel anticoagulant cofactor activity according to the present invention is based on the discovery of one patient with thrombosis and an abnormal APC-resistance when his plasma was assayed with the methods disclosed in WO 93/10261 (incorporated herein by reference) and by Dahlbäck et al. (Thromb. Haemost. 65, Abstract 39 (1991) 658). When studying a large cohort of patients with thrombosis, APC resistance was found to be the underlying cause in 30–40% of idiopathic thromboembolic events (Thromb. Haemost. 69, 999, abstract (1993)).

Later, it has been found, according to the present invention, that a crude fraction obtained from normal plasma contained an activity, which corrected the defect of APC-resistant plasma, whereas the corresponding fraction from APC-resistant plasma from a patient with pronounced APC-resistance was inactive. This proves the existence of a novel cofactor to APC. In addition, by using preparations purified in this activity in assays, which have been designed to measure this activity, conclusive evidence for the existence of a novel cofactor to APC has been achieved.

According to the present invention it has, thus, surprisingly been found that human Factor V has activity as a cofactor to APC, in addition to its well known function as a precursor to the procoagulant Factor Va. Possibly, this dual function of human Factor V is also expressed by Factor V derived from blood from some other animal species, especially mammals, but not expressed in other species. For instance, all results so far obtained indicate that bovine plasma is lacking the said activity.

The said cofactor activity of Factor V means that Factor V enhances the proteolytic effect of activated Protein C, thus promoting the degradation of Factor Va, i.e. the activated form of Factor V (FVa), as well as the degradation of Factor VIIIa.

It is previously well known that the procoagulant activity of Factor V is due to its activation by thrombin, in which three peptide bonds are cleaved, resulting in the formation of the procoagulant Factor Va as a complex between the N- and C-terminal portions of the native Factor V. The function of the two large activation peptides derived from the central portion of Factor V is, however, unknown. As will be shown in the experimental part of this disclosure, the APC-cofactor 2 activity has not been found for Factor Va in the APC-resistance test used.

Thus, the APC-cofactor 2 activity is preferentially expressed by the intact Factor V molecule, probably the large fragments cleaved off during activation thereof to Factor Va contributing to a major part of said activity. However, the possibility that the activity is associated with a molecular entity which forms a highly stable complex with Factor V, and which is not split under the purification procedures used to isolate the Factor V having APC-cofactor 2 activity, cannot be ruled out entirely. Accordingly, in connection with the present invention, the expressions "Factor V" and "Factor V having APC-cofactor 2 activity" and the like are intended also to encompass a Factor V complex and also fragments of Factor V, preferably other than the fragments originating from thrombin cleavage of Factor V, having the said activity. Modified Factor V with retained APC-cofactor activity may also be obtained through proteolytic cleavage by other enzymes of human or non-human origin such as snake venom enzymes and other proteases. Furthermore, the APC-cofactor 2 activity was found to remain after partial proteolysis by an unknown enzyme during the purification thereof, indicating a potential existence of APC-cofactor 2 active Factor V fragments. The expressions APC-cofactor 2 as well as Factor V having anticoagulant activity include fragments and subunits of Factor V/Va expressing the activity or an immunologic determinant related to a region associated with the said activity. Although, for the sake of convenience, coagulation factors and the like are not described by species of origin throughout this description, such factors are preferably of human origin unless otherwise specified.

In the experimental part of this disclosure, the procedures used for purification and characterization of the present novel APC-cofactor 2 activity are described, and its connection with Factor V is verified.

In summary, the evidence for the presence of the APC-cofactor 2 activity of Factor V is:

1. The procedure designed for the isolation of APC-cofactor 2 activity and earlier methods for the isolation of Factor V are very similar. On SDS-PAGE, three bands appear at approximately 200–220 kDa (C-terminal portion), 140–160 kDa (N-terminal portion) and 330 kDa, which is very similar to what has been previously reported for Factor V. (Compare the Examples below and Dahlbäck et al., J. Clin. Invest. 66 (1980) 583–91.) The intensity of the band at 330 kDa is enhanced for both APC-cofactor 2 activity and Factor V when higher concentrations of protease inhibitors are used during the purification procedure. For instance, a benzamidine hydrochloride concentration of 10 mM gives rise to a significant band at 330 kDa.

2. Specific polyclonal antiserum against human Factor V (Dakopatt A/S, Denmark) reacts with each of the three bands associated with APC-cofactor 2 activity in Western blotting.

3. After addition of thrombin to the preparations comprising APC-cofactor 2 activity, the three bands disappear and the products obtained become indistinguishable from the products formed by thrombin activation of Factor V.

4. Seventeen monoclonal antibodies reacting with Factor V have been obtained by using a preparation purified in respect of APC-cofactor 2 activity as immunogen. Two of the monoclonal antibodies partially inhibited APC-cofactor 2 activity without inhibiting Factor V procoagulant activity.

5. Factor V procoagulant activity and APC-cofactor 2 activity are coeluted on every chromatographic material tested: Heparin Sepharose, Blue-Sepharose, Wheat Germ Lectin Sepharose, Q-Sepharose and S-Sepharose (Pharmacia, Sweden).

6. Both Factor V procoagulant activity and APC-cofactor 2 activity are retained on a matrix carrying polyclonal antibodies against human Factor V (Dakopatts A/S, Denmark).

7. Both Factor V procoagulant activity and APC-cofactor 2 activity are retained on matrices, such as Sepharose and Affigel, carrying antisera against different fragments of bovine Factor V, which cross-react with human Factor V.

8. Both Factor V procoagulant activity and APC-cofactor 2 activity are retained and coeluted on a chromatographic support, such as Affigel, carrying a high affinity monoclonal antibody, which had been prepared by using a preparation purified in respect of APC-cofactor 2 activity as immunogen. In itself, this antibody inhibited neither APC-cofactor 2 activity nor Factor V procoagulant activity. Elution was performed at a pH of approximately 10.5–11.

9. A recent publication disclosing that autoantibodies against Factor V may result in thrombosis (Kapur et al., A. J. Hematol. 42 (1993) 384–388).

Preparations enriched in APC-cofactor 2 activity have been obtained by the same methods as have been used previously for the isolation of Factor V. It has been found that divalent metal ions, such as calcium ions, have a stabilizing effect on the APC-cofactor 2 activity and, hence, calcium ions were added during the purification.

Essentially the same purification procedure was used in an attempt to elucidate the novel activity as was disclosed in the above mentioned WO 93/10261. According to the results presented herein, the novel activity has been identified as a cofactor activity to APC expressed as a novel property of Factor V, or, possibly, a complex or fragments thereof as discussed above. Thus, alternative and simpler preparation methods will become available. Current methods, such as gel chromatography, affinity chromatography with e.g., anti-APC-cofactor 2 activity antibody, as affinity ligand, and ion exchange chromatography, etc., have been used, suitably after improvement to purify the novel activity described herein. In addition, methods based on DNA-recombinant technique may be applicable.

Accordingly, the present invention is also related to a preparation derived from blood or blood related products, such as plasma, said preparation being purified in respect of a blood coagulation component, which can express anticoagulant activity as a cofactor to APC thereby enhancing APC's proteolytic activity, directed against Factor $V_a$ and Factor $VIII_a$, said blood coagulation component being comprised of Factor V or, optionally, a stable complex of Factor V and a molecular entity, which can express said activity.

The normal plasma level of Factor V is approximately 10–20 μg/ml. By analogy to other blood coagulation/anticoagulation factors, the APC-cofactor 2 activity in 1 ml normal plasma is arbitrarily designated 1 unit (U).

The present invention is also concerned with antibodies and antibody preparations specific for a region of Factor V that is associated with APC-cofactor 2 activity, i.e., a region in which there is a site carrying an epitope either causing APC-cofactor 2 activity or APC-cofactor 2 inactivity. Such antibody preparations may be polyclonal, or preferably, monoclonal. Preferably, the antibodies of such preparations bind specifically to one or more Factor V sites associated with APCcofactor 2 activity. Alternatively, such a site could comprise an epitope involved in APC-cofactor 2 inactivity of Factor V and, thus, in APC-resistance. In connection with this invention the expression "epitope involved in APC-cofactor 2 inactivity" is meant to include an epitope related to decrease or loss of APCcofactor 2 activity.

Polyclonal antibodies can be obtained in accordance with known methods comprising immunization of a suitable animal, such as a mouse, rat, rabbit, dog, horse, sheep, goat, bird (e.g., hen, chicken, etc.), with a proper immunogen and recovery of the present antibodies from an appropriate fluid derived from said animal, e.g., from blood or serum in the case of mammals, or from eggs, when birds are immunized.

Preferably, the present antibodies are monoclonal antibodies which may be obtained by conventional methods, e.g., essentially as disclosed by Köhler, G. and Milstein, C., Nature 256, 495 (1975). Generally, a method to prepare monoclonal antibodies of the present invention includes immunizing a mammal, preferably a mouse, with a proper immunogen, producing hybrid cells by fusion of lymphocytes, such as splenic cells, from the immunized mammal with myeloma cells, selecting fused cells in a suitable medium, screening antibody-producing cells, cloning antibody-producing cells, i.e., hybridoma, and producing monoclonal antibodies in ascitic fluid of mice or, optionally, in a culture medium by propagation of the hybridoma therein. However, the present monoclonal antibodies, and fragments thereof binding to antigen, can also be obtained according to the methods based on recombinant technology, as is well known in this art. In such methods, suitable host cells of eucaryotic or procaryotic origin can be used. Such host cells are well known in this field of the art.

As immunogen, a purified preparation of Factor V, or fragments and derivatives thereof comprising the antigenic determinants responsible for expression of APC-cofactor 2 activity, can be used. Such fragments or derivatives may be conjugated to an immunogenic carrier, usually a protein, to become antigenic.

Using human Factor V deficient in APC-cofactor 2 activity (which can be obtained as described below) as the immunogen combined with a two-step screening procedure for selecting hybridomas producing monoclonal antibodies reactive with the immunogen but not with normal intact human Factor V, monoclonal antibodies reacting specifically with a human APC-cofactor 2 inactivity epitope, i.e., an epitope related to decrease or loss of APC-cofactor 2 activity, may potentially be obtained.

A preferred embodiment of the present invention is related to monoclonal antibodies that bind to and also inhibit APC-cofactor 2 activity of Factor V, at least in part. The present invention is also related to derivatives and fragments of such monoclonal antibodies, which are able to bind to antigens.

According to the present invention, monoclonal antibodies produced by mouse/mouse hybridoma are preferred, since these are simple to obtain. Illustrative of such monoclonal antibodies are those antibodies produced by a novel hybrid cell line deposited on Dec. 8, 1993 in the PHLS Centre for Applied Microbiology & Research, European Collection of Animal Cell Culture, Salisbury, Great Britain with the provisional accession number XAM-4-5-1 93120846. In connection with the present invention, monoclonal antibodies produced by this hybridoma are designated M4 (Master 4).

If not otherwise specified, the terms "antibody" or "antibody preparation" encompass the intact antibody with its two heavy and two light chains as well as different forms of derivatized antibodies containing the variable domains ($F_v$), e.g., fragments such as Fab, Fab', F(ab')$_2$; single chain antibodies; labelled antibodies, such as radiolabelled, fluorescent or enzyme-coupled antibodies; and antibodies bound to solid phases, etc.

A further embodiment of the present invention is concerned with antibody preparations, which comprise a definite number of monoclonal antibodies of the above-mentioned specificity, such as 1, 2, 3, 4, 5 or more different monoclonal antibodies. Such preparations may also be polyclonal. Polyclonal and monoclonal antibody preparations directed specifically against epitopes uniquely present in a site associated with APC-cofactor 2 activity are potentially useful in immunoassays for specifically determining the presence or absence of APC-cofactor 2 activity in a sample (quantitatively and qualitatively).

The present invention is also related to hybridomas that produce the monoclonal antibodies of the present invention, and preferably to the above mentioned hybridoma having the provisional accession number XAM-4-5-1 93120846.

Although polyclonal and monoclonal antibodies specific for Factor V, which can be used to purify Factor V, are previously known, monoclonal antibodies deliberately raised against a region of Factor V associated with APC-cofactor 2 activity have not been disclosed before.

The antibody preparations (monoclonal as well as polyclonal) of the present invention may, in most cases, be used in purification procedures based on affinity chromatography in which antibodies of this invention are attached to a solid carrier and used to selectively bind Factor V present, e.g., in a plasma preparation. Subsequently, Factor V bound to the solid carrier is eluted and collected.

The preferred monoclonal antibodies of this invention that bind to Factor V and inhibit, at least in part, APC-cofactor 2 activity of Factor V, can be used to inhibit said activity of Factor V. Such monoclonal antibodies may, like the previously known anti-Factor V antibodies, also be used to obtain plasma preparations deficient in APC-cofactor 2 activity.

Important aspects of the present invention are concerned with therapeutic methods, medicaments and pharmaceutical preparations, for which the knowledge of the novel anticoagulant activity of Factor V, i.e., APC-cofactor 2 activity, is used.

Accordingly, the present invention is also related to the use of Factor V, subunits or fragments thereof having anticoagulant activity as cofactor to APC for the manufacture of a medicament or pharmaceutical preparation intended for enhancing or restoring anticoagulant activity of APC in vivo. Specifically, such preparations are intended for treatment of patients suffering from, or predisposed to, vascular diseases, such as thromboembolic disorders including thrombosis and disseminated intravascular coagulation (DIC).

Such a medicament or pharmaceutical preparation may be comprised of a highly purified preparation of Factor V, which can be stored at low temperatures, such as −70° C.

The present preparations may also be used in connection with other conditions or situations in which an individual would benefit from a corrected or enhanced blood anticoagulant activity, for instance, in various clinical situations that are associated with increased risks for arterial and venous thrombosis.

Moreover, since the present APC-cofactor 2 activity is crucial for the effect of APC, this activity may be used by itself or in combination with Protein C/APC and/or Protein S. Clinical situations where this may prove to be important include patients being deficient in APC-cofactor 2 activity, in particular in situations increasing the risks for thrombosis. In addition, supplemental APC-cofactor 2 activity may be beneficial in connection with myocardial infarction, after thrombolytic therapy, in the post-operative period, in particular in high-risk patients, as an adjuvant to patients treated for thrombosis, in patients undergoing microsurgery, etc.

The administration route for APC-cofactor 2 activity is that normally applied for therapy with blood coagulation/anticoagulation factors, such as intravenous or intra-arterial injection or infusion. As has been suggested for other blood factors, oral administration can not be excluded. The amount to be administered shall be effective in the sense that, at least for a period of time, it fully or partially restores the effect of the patient's own activated Protein C or the effect of co-adminstered Protein C/activated Protein C, with the understanding that even smaller effects may be beneficial to a patient at risk of thrombosis. An amount in the range of 1–100, possibly 40–70, mg/day, can be assumed to be useful. Repeated administration is preferred, because Factor V expressing APC-cofactor 2 activity is metabolized in the mammalian body.

The different types of pharmaceutical compositions applicable are the same as in use for other blood coagulation/anticoagulation factors, but adapted to the specific stability requirements that are necessary for Factor V having APC-cofactor 2 activity. For instance lyophilized or spray dried powders, optionally diluted with appropriate vehicles, as well as sterile or aseptically produced aqueous solutions can be used.

A further aspect of the present invention is related to the use of Protein C/activated Protein C and/or Protein S for the manufacture of a pharmaceutical composition for the treatment of disorders related to deficiency in APC-cofactor 2 activity. The same types of compositions as intended for the prior art therapeutic use of Protein C and Protein S are applicable.

Another aspect of the present invention is related to a Factor V preparation deficient in APC-cofactor 2 activity and is preferably derived from humans. A potential therapeutic use thereof is in cases where an increase in Factor Va activity over APC-cofactor 2 activity is beneficial to a patient.

The above-mentioned therapeutic methods and preparations are intended for mammals, particularly humans.

The novel anticoagulant cofactor activity according to the present invention can be used to develop methods for diagnosing such blood coagulation/anticoagulation disorders that are related to the functional activity of APC, and also to develop methods for monitoring and/or measuring functional activities of components involved in the blood coagulation/anticoagulation system, that directly or indirectly depend on the functional activity of APC.

Accordingly, a suitable embodiment of the present invention is related to a method for diagnosing a blood coagulation/anticoagulation disorder, preferably a thromboembolic disorder, or determining predisposition therefor, in an individual, preferably a mammal, such as a human being, said method comprising determining in a sample, preferably a blood or blood derived sample, such as plasma, derived from said individual, the level of a blood component expressing anticoagulant activity, said blood component comprising Factor V, where in the level of its anticoagulant activity as a cofactor to APC is determined, an abnormal, preferably a decreased, level indicating manifestation of or predisposition to said disorder in particular for a decreased level said disorder being a thromboembolic disorder.

Suitable embodiments of the above method are related to assaying the appropriate sample from an individual for Protein C/APC, Protein S or APC cofactor 2 activity, and relating an observed abnormal level, preferably a lowered level, to a diagnosis that the individual has a blood coagulation disorder related to the assayed factor (i.e., to activated protein C/Protein C, Protein S, or Factor V in its capacity as APC-cofactor 2), which defect may be an underlying cause for a thromboembolic disorder, or predispose to said disorder.

In the above methods, the level of the anticoagulant APC-cofactor 2 activity is preferably measured in accordance with methods developed according to the present invention for assaying functional APC-cofactor 2 activity that are described below. Immuno-based activity assays and non-functional assays specific for Factor V carrying structural elements associated with its APC-cofactor 2 activity can also be used.

Thus, further aspects of the present invention are related to functional assays for activated Protein C/Protein C, Protein S, and Factor V expressing APC-cofactor 2 activity and also to immune assays, nucleic hybridization assays, and DNA and RNA sequencing methods for Factor V expressing APC-cofactor 2 activity.

These assays, as such, may have other uses than as diagnostics. For instance, the disclosed assays may be useful in monitoring purification procedures of components in the APC-cofactor system, and standardising control plasmas, etc.

A. Functional Assays of APC Protein C, APC-Cofactor 2 Activity and Protein S.

These assays utilize similar protocols as described earlier (Bertina et al., Res. Clin. Lab. 20 (1990) 127–138; Wolf et al., Thromb. Haemost. 62 (1989) 1144–1145; WO 91/02812; WO 91/01382; WO 93/10261; Dahlbäck et al., Thromb. Haemost. 65, Abstract 39, (1991) 658).). The method disclosed in the US designation of WO 93/10261 (USSN 199328, issued on Aug. 25, 1995 as U.S. Pat. No. 5,443, 960), which has been incorporated by reference, comprises the following steps:

(i) a plasma sample obtained from the individual is incubated with (a) an exogenous Reagent (I) activating at least partially the blood coagulation system of the sample, and with (b) activated exogenous Protein C (APC) or exogenous PC together with exogenous Reagents (II) that transform PC to APC, and (c) further components, such as $Ca^{2+}$ salt and phospholipid or tissue thromboplastin, that are necessary for efficient reaction of the activated factors introduced according to step (i:a), and (d) if desired, an exogenous substrate for an enzyme which activity is influenced by activated Protein C;

(ii) a substrate conversion rate is monitored directly for a blood coagulation enzyme which activity is influenced by activated Protein C, (iii) the conversion rate determined in step (ii) is compared with a standard value being obtained from steps (i)–(ii) under identical conditions for plasma of normal individuals.

As taught in U.S. Pat. No. 5,443,960, in cases where the substrate conversion rate is not normal compared to the standard, the individual from which the sample derives is classified as suffering from the disorder or being at risk for acquiring the disorder. An increased conversion rate of the sample indicates a thromboembolic disease or a risk for such a disease (with fibrinogen as the substrate an increased conversion rate means a shortened clotting time). The significance of a lowered conversion rate is at the present stage not known (with fibrinogen as the substrate a lowered conversion rate means a prolonged clotting time). Probably it is not related to any disease. The range of the normal conversion rate may be quite broad. Hence, it might, as a complement, be of value to run steps (i)–(ii) on a plasma sample from the individual with exclusion of the incubation according to (i:b) and compare the result obtained with that obtained.

In accordance with the present invention, a component in the system of APC, Protein S and Factor V, the latter in its capacity as APC-cofactor 2, is assayed from the conversion of the appropriate APC substrate by APC. Normal APC substrates are Factors $V_a$ and/or $VIII_a$, one or both of which preferably are added to the assay medium as enriched, or highly purified preparations, including preparations by recombinant technology, of unactivated (Factor V, Factor VIII) or activated proteins. Within a series of samples that are to be compared, the assay media have essentially the same levels of:

(a) at least one of Factor V having APC-cofactor 2 activity or an inhibitor that blocks the same sample derived activity, and Protein S or an inhibitor that blocks sample derived Protein S activity, when APC or Protein C is to be assayed;

(b) at least one of Protein S or an inhibitor that blocks sample derived Protein S activity, and APC, when APC-cofactor 2 activity is to be assayed; and (c) at least one of Factor V providing APC-cofactor 2 activity or an inhibitor that blocks the same sample derived activity, and APC, when Protein S is to be assayed.

Accordingly, the final assay media for a series of samples which are to be compared contain sample and substrate for APC, and optionally one or two, preferably two, substances that do not derive from the sample and that are selected from APC, Protein S or an inhibitor to Protein S, and Factor V having APC-cofactor 2 activity or an inhibitor to this activity, with the proviso that one of the remaining substances is the entity to be assayed (i.e., APC, Protein C, Protein S or APC-cofactor 2 activity).

The present method may comprise a) incubating in one or more steps in an aqueous assay medium, the sample and a substrate for APC, said substrate being inherently present in the sample or added to the assay medium, and optionally further blood coagulation components inherently present in the sample or added to the assay medium, b) measuring the conversion of the substrate caused by APC during the incubation according to a), and c) correlating the measured value in a known manner to the activity to be determined. In this method, optionally, one or two, preferably two, substances selected from APC, Protein S or a Protein S inhibitor, and Factor V having anticoagulant activity or an inhibitor to said activity are added to the assay medium of a), with the proviso that one of the remaining substances (i.e., APC, Protein S or APC-cofactor 2 activity) is present in the sample and is the component, the functional activity of which is to be determined (e.g., for Factor V, the activity being anticoagulant activity as cofactor to APC).

Illustrative of other components that may be present are coagulation enzymes and other blood factors enabling the measurement of the degradation of Factors $V_a$ and/or $VIII_a$. These other factors may be added separately or may be present already in the sample. In case the sample contains Protein C, and APC is to be assayed, an activator for Protein C must be added. In case the sample contains varying levels of coagulation factors (other than the one to be assayed) interfering with the assay reactions, one should secure excess of them (i.e. essentially constant levels in the assay media) in order to avoid inter-sample variations in the test results. For plasma samples, constant levels may be accomplished by adding, in excess, normal plasma deficient in the entity to be assayed. The components to be added may also be in enriched or highly purified forms. It can be envisaged that addition of Factor VIII/$VIII_a$ and/or forms of Factor V not expressing the APC-cofactor activity is suitable. Examples of forms that lack APC-cofactor activity are human Factor V deficient of the activity, Factor V from a species not normally expressing the activity (for instance bovine Factor V, and Factor V fragments expressing Factor V activity but not APC-cofactor 2 activity).

The addition of Protein S in the assay medium is done in order to avoid variations in the measured level caused by intersample variations in Protein S, when APC-cofactor 2 activity or Protein C is to be measured. When Protein S is to be measured, APC-cofactor 2 activity may be added for the same purpose. The purpose of this is to keep the functional activity level of factors other than the one to be determined essentially constant in the assay media on an inter-run basis. As previously indicated, this may be accomplished by including into the assay media such factors in excess, for instance by adding normal plasma in excess, and/or by including functional excess of inhibitors for such factors, for example antibodies binding to epitopes responsible for the activity of such factors. Thus, a monoclonal antibody specific to the epitopes responsible for the APC-cofactor activity of Protein S has been successfully included (HPS 54, Dahlbäck et al., J. Biol. Chem. 265 (1990) 8127–8235) in assay media for assaying APC-cofactor 2 activity. Similarly, functional inhibitors for APC-cofactor 2 activity, like the above-mentioned monoclonal antibodies, may potentially be included in assay media when Protein S is to be assayed.

According to the present invention the functional assays are suitably performed in presence of added Factor VIII/VIII$_a$.

The principles for the order of mixing, components to be added and the different measuring principles are well-known in the field. See the above-mentioned citations. Thus, APC activity may be followed by addition of substrates such as fibrinogen (clotting assays) and chromogenic substrates for coagulation enzymes, the activity of which are influenced by APC activity. Suitable chromogenic, fluorogenic and luminogenic substrates are thus thrombin and Factor X$_a$ substrates.

The sample is normally plasma from an individual/patient, or the sample may be Factor V having APC-cofactor 2 activity, Protein C (APC) or Protein S, all of these derived from a manufacturing process, or standards to be used in the assay.

Native Factor V (abbreviated FV) produced through recombinant technology (rFV) may be used instead of FV purified from plasma as an adduct in diagnostic methods for Protein C/APC or Protein S, as a standard or control in assays for FV anticoagulant activity, or as a therapeutic agent for administration to patients partially or completely deficient in APC-cofactor 2 activity. Alternatively, recombinant variants or fragments of FV with modified expressions of procoagulant or anticoagulant activity may be utilized for the same purposes and also as adducts in methods for FV anticoagulant activity. Such modifications may be generated through mutations of the thrombin or APC cleavage sites in FV. In the former case the procoagulant activity, and in the latter case the anticoagulant activity of FV, is partially or completely lost. Furthermore, such species, or suitable immunogenic peptide fragments thereof, may be used for preparation of monoclonal antibodies for diagnostic or therapeutic use.

In assays for APC-cofactor 2 activity utilizing Factors V$_a$ and/or VIII$_a$ as the APC substrate and factors from the sample to measure APC substrate conversion, the sensitivity towards APC activity is considerably increased in plasmas from patients on treatment with vitamin K antagonists, resulting in an enhanced prolongation of clotting time in certain clotting assays, especially APTT tests. The increased sensitivity towards APC activity may be explained by the lowered levels of vitamin K-dependent proteins such as Factors IX, X and II. Since APC-cofactor 2 activity is not vitamin K-dependent, it may therefore become possible to measure this activity in plasmas from such patients by exogenous addition to the assay medium of certain vitamin K-dependent protein(s), such as at least one of Factors IX, IX$_a$, X and II, optionally combined with Protein S. These proteins may be added in the form of heavy metal salt eluate, such as a barium citrate eluate (Dahlbäck, Biochem. J. 209 (1983) 837–46) or aluminium hydroxide eluate (Bertina et al., Thromb. Haemost. 51 (1984) 1–5) or as purified components before measuring the APC substrate conversion. If the plasma contains heparin (standard or of low molecular weight) it is suitable to neutralize this effect by adding excess of heparin, or by adding polybrene or Protamine, or the like, as heparin inhibitors to reduce interference with the assay results.

As stated above, the present methods for determining functional activities of PC/APC, Protein S, or Factor V anticoagulant activity are similar to methods described earlier, e.g., in the cited references, the disclosure of which is included herein by reference. Thus, a detailed description of these methods should not be required. In principle, however, such methods are based on measurement of conversion of a substrate, the rate of which can be directly or indirectly determined and related to the substance to be assayed, e.g., based on coagulation or chromogenic assays, suitably in presence of further components necessary to detect the conversion rate, which are inherently present in, or added to, the sample.

Such components may comprise a reagent that serves to introduce an activated coagulation factor that can be used for determination of the substrate conversion rate. This reagent leads to the presence of at least Factor IX$_a$, and may comprise a certain coagulation factor or a reagent that activates the system via the intrinsic or extrinsic pathway. Accordingly, this reagent may be Factor IX$_a$ or Factor XI$_a$, (intrinsic pathway), Factor XII$_a$ (intrinsic pathway), kallikrein (intrinsic pathway), a contact activator (intrinsic pathway) such as kaolin, celite or ellagic acid (intrinsic pathway), an APTT reagent (Activated Partial Thromboplastin Time; i.e., a reagent containing a phospholipid and a contact activator (intrinsic pathway)), tissue thromboplastin (PT-reagent, PT=Prothrombin time (extrinsic pathway)), tissue factor, Factor VII$_a$ and Factor X$_a$.

Other components that can be added, depend on the mode employed and may necessitate the inclusion of plasma protease inhibitors for enzymes other than the monitored one or the inclusion of a fibrin polymerization inhibitor. Ca$^{2+}$ may be in the form of a plasma soluble salt that provides the Ca$^{2+}$ ion in free uncomplexed form, i.e., strong Ca$^{2+}$ ion in free uncomplexed form. Such additional components suitably also include Factor VIII/VIII$^a$ and Factor V/V$_a$.

The substrate for which the conversion rate is determined may comprise a synthetic substrate for an enzyme, the activity of which is influenced by activated Protein C, for example thrombin (Factor II$_a$) and Factor X$_a$. Suitable synthetic substrates are water soluble and preferably have an oligopeptide structure with three, four or five amino acid residues and an amino terminus that is protected from being attacked by amino peptidases. The protection is accomplished either by a protecting group or by having a D-amino acid at the amino terminus. In order to give a detectable response, the carboxy terminus of a synthetic substrate is amidated with a group that specifically can be released and detected upon action of the relevant blood coagulation protease. The group to be released is selected among chromogenic, fluorogenic or chemiluminogenic groups and other analytically detectable groups. See further H. C. Hemker, "Handbook of Synthetic Substrates for the Coagulation and Fibrinolytic System", Martinus Nijhoff Publishers, 1983, and J. Fareed et al., "Synthetic Peptide Substrates in Hemostatic Testing" in CRC Critical Reviews in Clinical Laboratory Sciencies Vol 19, Issue 2, 71–134 (1983). In the case of samples other than plasma samples, exogenous fibrinogen may be added as substrate.

In order to accomplish a specific result with respect to the substance to be determined, in some cases one should try to keep the plasma sample content of the final assay medium as high as possible. Accordingly, a plasma sample content in tests having good specificity could be >10%, in particular >20% or >35% (v/v). In other cases, however, an essentially lower content, that is below 10% (v/v), can be used.

B. Immune Assays for APC-Cofactor 2 Activity.

The antibody preparation of the invention will enable immune assays of APC-cofactor 2 activity, wherein anti-APC-cofactor 2 antibody is allowed to form an immune complex with Factor V having APC-cofactor 2 activity in the sample in an amount that is a qualitative or quantitative measure of the APC-cofactor 2 activity level in the sample. The samples may be the same as for functional assays. The present invention is also concerned with reagents for use in assays described herein.

Purified preparations comprising Factor V expressing the APC-cofactor 2 activity, which has been purified from plasma or prepared by recombinant technology, Protein C preparations, optionally in an activated form or combined with a Protein C activator, and Protein S preparations, which contain defined amounts of their respective factor may be used as a reagent, a standard or a control in the above-mentioned assays. The Protein C preparation may be combined with at least one vitamin K dependent coagulation factor selected from Factors IX, X and II, and optionally combined with Protein S. Products and preparations for therapeutic use may also be obtained by recombinant technology. Furthermore, the present monoclonal antibodies may be obtained by recombinant technology, and essentially PCR-technology, which is well known, may be used to obtain such antibodies having desired specifity.

There are indications that information may be obtained about various Factor V mutations based on interactions between Factor V anticoagulant activity and Protein S. Methods may be designed to obtain such information in the presence or absence of a suitable antibody. Such methods in the presence of antibody may be used as a quantitative method for an analyte, such as Factor V anticoagulation activity and Protein S.C.

C. Hybridization Assays.

Recent results have shown in a conventional DNA-linkage study of a large family with inherited APC resistance that there is a strong linkage between a neutral polymorphism in the Factor V gene and expression of APC-resistance. This strongly suggests that a mutation in the Factor V gene is the cause for APC-resistance. This is conclusive evidence that nucleic acid hybridisation assays, as well as nucleic acid sequencing can be used in conventional ways in order to detect individuals at risk for thrombotic events due to a low level of APC-cofactor 2 activity. Thus, these types of assays may be used for checking, in an individual, the abnormal presence or absence of one or more nucleic acid fragment(s) and/or sequence(s) unique for the presence or absence of expression of a Factor V molecule either carrying APC-cofactor 2 activity or being deficient in this activity. The protocols and conditions are the same as normally applied for other genes, except for now using reagents specific for the Factor V gene and, optionally, mutation(s) associated with APC-resistance or specific for a normal Factor V gene. Any cell sample from the individual may be appropriate.

Furthermore, the present invention is concerned with Factor V, suitably human Factor V, capable of becoming activated to exert Factor Va procoagulant activity but not capable of exerting anticoagulant activity, preferentially not anticoagulant activity as a cofactor to APC, said factor being in a substantially pure form.

Another aspect of the invention is related to Factor V, suitably human Factor V, capable of exerting anticoagulant activity, preferentially as a cofactor to APC, but not capable of expressing procoagulant activity of Factor $V_a$.

Such Factors can be purified from plasma with methods similar to normal Factor V, or prepared by recombinant technology. Possible applications are in standards and as supplementing reagents, and for therapeutic use.

EXAMPLES

Assay for APC-Cofactor 2 Activity:

A modification of the recently described APC-APTT method (PCT/SE/9200781; and Dahlbäck et al., Proc. Natl. Acad. Sci. USA, 90 (1993) 1004–1008) was developed to measure APC-cofactor 2 activity during its purification. The method used plasma from an individual which had an inherited poor response to APC and fractions obtained from normal plasma which were tested for their ability to normalize the poor APC response. The assay which will be referred to as APC-cofactor 2 activity assay was performed as follows: 50 µl plasma demonstrating a poor response to APC (referred to as APC-resistant plasma) was incubated with 50 µl of the test fraction and 50 µl of an activated thromboplastin time (APTT) reagent (APTT-automated Organon Technica (USA)) for 5 minutes at 37° C. before coagulation was initiated by the addition of 5 µl of an APC-CaCl$_2$ mixture (if not indicated otherwise, 20 nM human APC in 10 mM Tris-HCl, 0.05 M NaCl, 30 mM CaCl$_2$, pH 7.5, containing 0.1% bovine serum albumin (BSA)), and the coagulation time was measured. The presence of APC-cofactor 2 activity in a test sample is associated with an increase in clotting time.

Each example was also analyzed in parallel without the addition of APC to the CaCl$_2$ solution and the APC-dependent prolongation of clotting time was calculated. To construct a dose-response curve for APC-cofactor 2 activity, the plasma deficient in APC-cofactor 2 activity was mixed with control plasma and used as test-plasma in the APC-APTT method. The anti-coagulant response of APC was related to the percentage of control plasma and the curve had an exponential shape. As it was unknown whether the plasma deficient in APC-cofactor 2 activity was completely devoid of Factor V expressing APC-cofactor 2 activity, the assay only provided a semi-quantitation of the cofactor in different fractions. However, the assay served the purpose of providing a means to follow the APC-cofactor 2 activity during its purification.

A Factor V clotting assay was performed using Factor V-deficient plasma as described previously (J. Clin. Invest. 66, 583–591 (1980)). The presence of Factor V activity resulted in a shortening of clotting time of the deficient plasma. In both the APC-cofactor 2 activity assay and Factor V clotting assay the original clotting data have been shown rather than the results converted into units.

Electrophoretic, Immunological and Other Methods: Gradient (5–15%) polyacrylamide slab gel electrophoresis in the presence of sodium dodecyl sulfate (SDS-PAGE) and Western blotting were performed using techniques previously described (J. Biol. Chem. 261, 9495–9501 (1986)). A specific rabbit polyclonal antiserum against Factor V was the kind gift of Dakopatts A/S. Data demonstrating the specificity of the antiserum have been reported previously (Blood 68, 244–249 (1986)). Rabbit polyclonal antibodies were raised against the isolated heavy and light chain fragments of bovine Factor V (J. Biol. Chem. 261, 9495–9501 (1986)). Monoclonal antibodies were raised using standard methods, as previously described in detail (J. Biol. Chem. 265, 8127–8135 (1990)). The purified protein in the S-300 pool was used as antigen in the immunization of Balb/c mice. Seventeen different antibodies were obtained and their reactivities tested with Western blotting. Approximately 20 mg of an antibody designated Master 30 was coupled to 4 ml Affigel 10 (Biorad) in accordance with the manufacturer's instructions. IgG-fractions of the polyclonal antisera against human Factor V and the bovine Factor V fragments were also coupled to Affigel (approximately 5 mg/ml).

Purification of APC-Cofactor 2 Activity:

All manipulations of samples were performed on an ice bath; chromatographies and centrifugations were run in the cold room, suitably at 4° C. Blood-collection: Human freshly frozen (–70° C.) citrated plasma was obtained from the local blood bank. The frozen plasma (2.3 L) was thawed at 37° C. and the following protease inhibitors were added: phenylmethanesulfonyl fluoride (PMSF) (1 mM), diisopropylfluorophosphate (DFP) (1 mM), soy bean trypsin inhibitor (50 mg/L), Trasylol (aprotinin) (1.5 mg/L which is equal to 10 units/ml), and benzamidine (10 mM). The plasma (kept on an ice-bath) was subjected to barium-citrate adsorption as previously described (Dahlbäck, Biochem. J. 209 (1983) 837–846) and the barium-adsorbed plasma was subjected to fractionated polyethylene glycol precipitation (PEG 6000) (8% w/v) by the addition of solid PEG. The APC-cofactor activity was recovered in the 8% PEG supernatant. The 8% PEG supernatant was diluted with an equal volume of 10 mM benzamidine and then mixed with Q-Sepharose (Pharmacia LKB Biotechnology, Uppsala, Sweden) and equilibrated in 20 mM Tris-HCl, 0.1 M NaCl, 1 mM $CaCl_2$, pH 7.5, comprising 10 mM benzamidine. After 1 hr of gentle mixing, the gel was collected in a Buchner funnel and washed with A, 3 L equilibration buffer, B, 1 L equilibration buffer with 0.1% Tween 20 and C, 2 L equilibration buffer containing 0.15 M NaCl instead of 0.1 M NaCl. The gel was then packed in a column (5 cm diameter) and the adsorbed proteins were eluted with a linear gradient of NaCl (0.15–0.5 M NaCl in 20 mM Tris-HCl, 1 mM $CaCl_2$, 10 mM benzamidine, pH 7.5, 1.5 L in each gradient vessel). The flow rate was 330 ml/h and 11 ml fractions were collected. Fractions were analyzed for APC-cofactor 2 activity and Factor V activity in 1/10 dilutions (FIG. 1).

Fractions were pooled as indicated by the horizontal bar and subjected to $(NH_4)_2SO_4$ precipitation (70% saturation). The precipitate was collected by centrifugation, dissolved in a minimal volume of 20 mM Tris-HCl, 0.15 M NaCl, 1 mM $CaCl_2$, pH 7.5, containing 10 mM benzamidine, 1 mM DFP, and 1 mM PMSF and applied to a column (2.5 cm×93 cm) with Sepharcryl S-300 (Pharmacia, Uppsala, Sweden) equilibrated in the same buffer but without DFP and PMSF. The column was run at 10 ml/h and 1.2 ml fractions were collected. The fractions were analyzed with APC-cofactor 2 activity assay and Factor V assay at 1/10 dilutions (FIG. 1). Fractions were pooled as indicated by the horizontal bar and stored at –70° C.

Affinity Chromatography Using Monoclonal Antibodies

The protein obtained as described above from an S-300 chromatography (in the illustrated run approximately 6 mg in 20 mM Tris-HCl, 0.1 M NaCl, 2 mM $CaCl_2$, pH 7.5) was applied to a column (0.75 cm×7.5 cm) of Affigel with immobilized monoclonal antibody designated Master 30, the column and protein being equilibrated in 20 mM Tris-HCl, 0.1 M NaCl, 2 mM $CaCl_2$, pH 7.5. After washing the column until absorbance of the eluate reached zero, bound proteins were eluted with 50 mM diethanolamine, 2 mM $CaCl_2$, pH 10.6. The pH of the eluate was immediately neutralized with 3 M Tris-HCl, ph 7.5 (50 µl per 1 ml fraction). The fractions were analyzed (at 1/5 dilution) with APC-cofactor 2 activity assay and Factor V clotting assay. Active fractions were pooled, concentrated by ultrafiltration (YM10 membranes) and stored at –70° C. The purified APC-cofactor 2/Factor V was activated with thrombin as described previously (J. Clin. Invest. 66, 583–591 (1980)).

Preparation of Monoclonal Antibodies

The purified protein, i.e., Factor V (APC-cofactor 2), was used as an immunogen for the immunization of Balb/c mice in accordance with a standard protocol. Splenic cells from said mouse were fused with cells of the Sp 2/0 Ag14 mouse myeloma cell line and selected in hypoxanthine-aminopterin-thymidin DMEM medium as disclosed by Köhler and Milstein (supra).

A solid phase enzyme-linked immunosorbent assay (ELISA) was used to detect antibodies produced against Factor V in antisera from the mice as well as to detect antibody-producing hybrid cells. In those assays, Factor V (10 µg/ml in standard coating buffer) was coated in wells on microtiter plates. Antisera from immunized mice and supernatants of the hybrid cell cultures were added in dilution to the wells and individual wells were assayed for the presence of antibodies bound to Factor V with the aid of an enzyme-labelled secondary antibody by standard methods.

Hybrid cells from positive wells, i.e., antibody-producing cells, were cloned by limiting dilution, subcloned and expanded. After implantation in the abdominal cavity of pristane pretreated mice, monoclonal antibodies were produced in ascitic fluid in large amounts.

Seventeen masters were obtained, all of which reacted with antigenic determinants on Factor V as shown in accordance with the Western blot method, the majority of these monoclonal antibodies (abbreviated Mab's) being directed to the same region of Factor V, namely, the activation fragment comprising the central 150 kDa region of Factor V.

One of these Mab's, designated Master 30, was used for the affinity purification of Factor V as described above. The Mab's described above were tested to determine their influence on coagulation activity and APC-cofactor 2 activity in plasma.

Increasing amounts of purified Mab up to 400 µg/ml were added to normal plasma and after incubation (15–30 minutes), the activity of Factor V was measured with a conventional Factor V assay based on coagulation analysis, and the response to exogenous APC was determined according to the following.

Normal plasma samples comprising varying concentrations of Mab (10–400 µg/mL) were incubated with a commercial APTT reagent. (In the present tests Automated APTT from Organon was used. Similar results were obtained with the APTT reagent from COATEST APC Resistance, Chromogenix AB, Mölndal, Sweden.) After incubation for 5 minutes at 37° C. either 30 mM $CaCl_2$ (in 20 mM Tris-HCl, 50 mM NaCl, pH 7.5 comprising 0.1% bovine serum albumin (BSA)) or activated Protein C (APC) (about 2 μg/ml in 30 mM $CaCl_2$ dissolved in 20 mM Tris-HCl, 50 mM NaCl, pH 7.5 comprising 0.1% BSA) was added and the clotting times were recorded. The APTT assay was performed essentially as disclosed by Dahlbäck et al., PNAS 90 (1993) 1004–1008.

The presence of these Mab's either had no effect on the conventional APTT time, i.e. the clotting time, obtained for samples comprising added $CaCl_2$, or had only a moderate effect, with clotting times of 40–45 seconds being observed. Two of the Mab's, designated Master 1 and Master 4, were, however, found to shorten the clotting time for samples, to which APC in a $CaCl_2$ solution had been added, (APC time).

The following clotting times were obtained:
APC time in the absence of Mab's 110–120 seconds
APC time in the presence of Master 4 80–90 seconds.

These results indicate an inhibition in part of the APC-cofactor 2 activity in plasma in the presence of Master 4. This partial inhibition activity of Master 4 was found to be dependent on the added amount, maximal inhibition being obtained when 50–100 μg of Master 4 per ml plasma were added. Master 4 has been deposited as stated above.

The results from the above tests are discussed below with reference to the Figures.

FIG. 1 illustrates chromatography on Q-Sepharose (A) and Sephacryl S-300 (B) of factor V and APC-cofactor 2 activity. On both columns, the elution profile of APC-cofactor 2 activity (upper sections) coincided with that of Factor V (middle sections). Factor V activity was demonstrated as a shortening of clotting time of Factor V-deficient plasma, whereas APC-cofactor activity was associated with an APC-dependent prolongation of clotting time of APC-resistant plasma. The fractions were pooled as shown by the horizontal bars.

Figure 2:
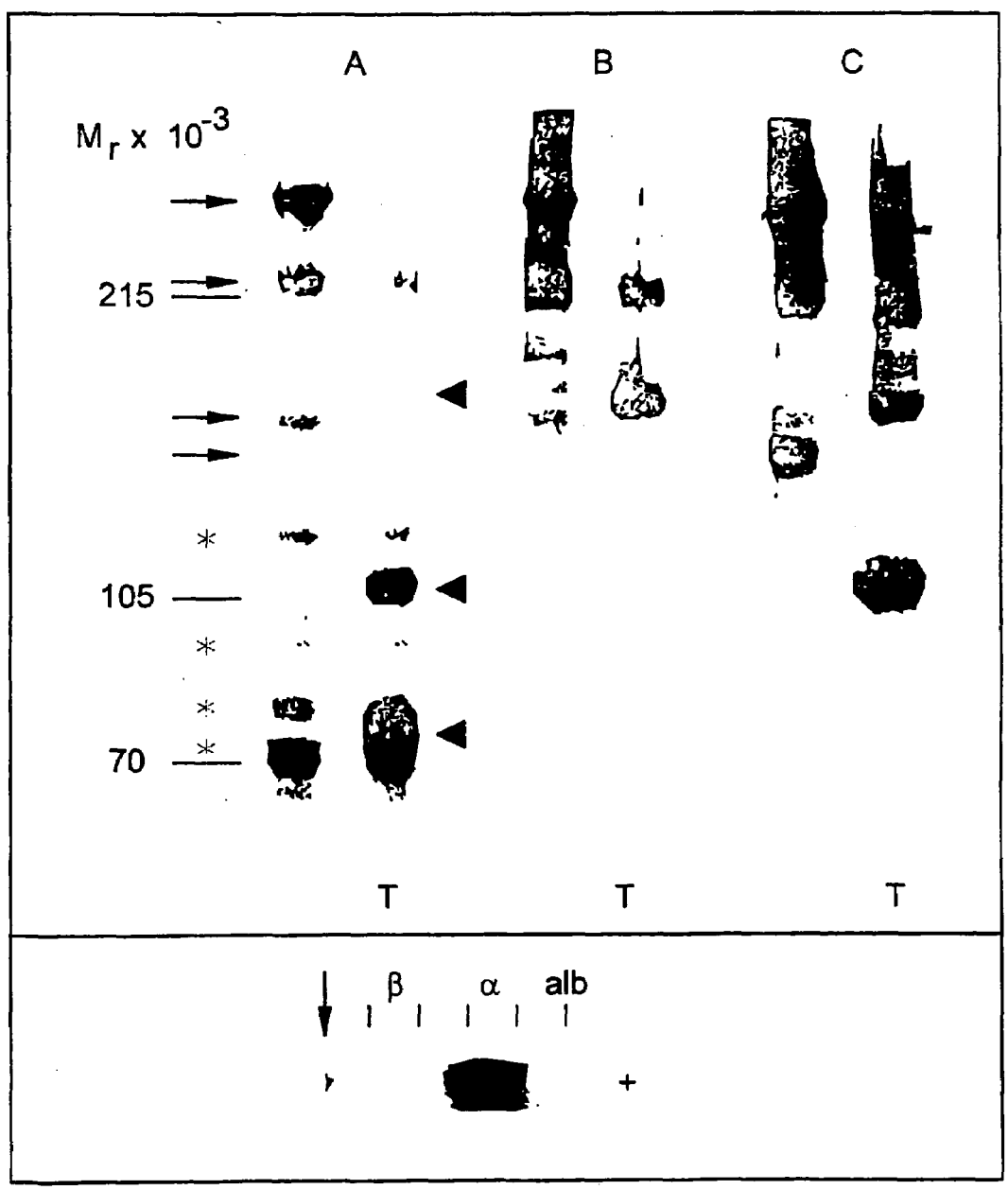
FIG. 2 illustrates the results from characterization of isolated APC-cofactor 2 activity/Factor V on SDS-PAGE, Western blotting, and agarose gel electrophoresis.

FIG. 2 illustrates the results from characterization of isolated APC-cofactor 2/Factor V on SDS-PAGE, Western blotting, and agarose gel electrophoresis. The pool from the S-300 column was analyzed by SDS-PAGE, before and after incubation with thrombin. The gels were either stained with Coomassie blue (A) or subjected to Western blotting using monoclonal antibody (Master 30) (B) or polyclonal (C) antibodies. Samples applied to the SDS-PAGE were reduced; approximately 20 μg protein was applied to each lane in the protein-stained gel, whereas approximately 1 μg was applied to each of the lanes used for Western blotting. Lanes with thrombin-cleaved protein are marked T. Positions of molecular weight markers are given to the left. Factor V-related polypeptides are marked with arrows, whereas fragments formed by thrombin (J. Biol. Chem. 257, 6556–6564) are indicated by arrowheads. The 150 kDa fragment stains poorly with Coomassie, but is readily observed on Western blotting. Intermittently observed bands are denoted by asterisks. The S-300 pool was also analyzed by agarose gel electrophoresis (bottom section). The positions of albumin (alb), $α_1$, $α_2$, $β_1$ and $β_2$ bands of a plasma control are indicated by vertical lines.

Figure 3:
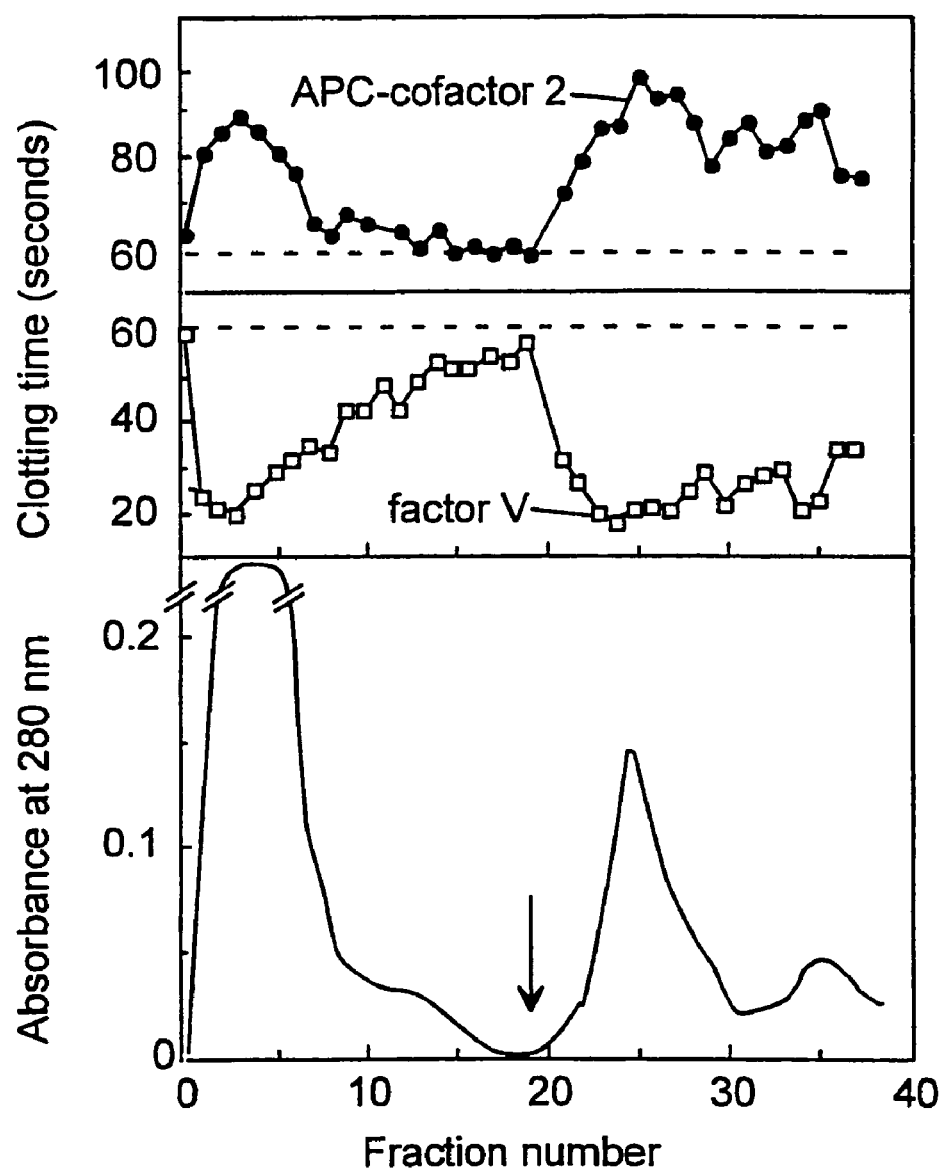
FIG. 3 illustrates co-purification of APC-cofactor 2 activity and Factor V on monoclonal antibody affinity chromatography.

FIG. 3 illustrates copurification of APC-cofactor 2 activity and Factor V on monoclonal antibody affinity chromatography. The S-300 pool was applied to monoclonal antibody (Master 30) affinity chromatography. As the binding capacity of the column was exceeded, most of the protein passed through the column. After washing the column, the bound protein was eluted with high pH (start of elution indicated by arrow). Fractions were analyzed with both APC-cofactor 2 activity and Factor V assay. Factor V activity was associated with a shortening of clotting time of Factor V-deficient plasma, whereas APC-cofactor activity gave an APC-dependent prolongation of clotting time of APC-resistant plasma. The two dashed lines represent clotting times of buffer controls.

FIG. 4. A–B illustrates correction of APC-resistance by purified APC-cofactor 2/Factor V. Affinity purified APC-cofactor 2/Factor V (at indicated concentrations in a volume of 50 ul) was mixed with APC-resistant plasma (50 ml). The mixtures were then tested in the APC-cofactor 2 activity assay (A) with (●) and without (○) APC in the $CaCl_2$-solution, and in the Factor V assay (B). Each point represents the mean of duplicate measurements.

Results

APC-cofactor 2 activity was analyzed with a biological assay using plasma from an individual (designated AS-plasma) with APC-resistance as test plasma, and a procedure was devised for purification of APC-cofactor 2 from normal plasma. The first step in the procedure was barium-citrate adsorption, which removed the vitamin K-dependent proteins including Protein C and Protein S. The barium-citrate eluate had no APC-cofactor 2 activity. On fractionation of the supernatant plasma with PEG 6000 precipitation, the APC-cofactor 2 activity was present in the 8% PEG supernatant, whereas the dissolved 0–8% PEG 6000 precipitate had no APC-cofactor 2 activity. The APC-cofactor 2 activity in the 8% PEG supernatant was purified first by anion exchange chromatography on a column with Q-Sepharose and then by gel filtration on Sephacryl S-300 (FIG. 1). This purification protocol was very similar to a procedure for purification of coagulation Factor V (J. Clin. Invest. 66 583–591 (1980)), and Factor V was found in the same fractions of APC-cofactor 2 activity. The purification was performed at least 10 times with different modifications, and the elution profiles for Factor V and APC-cofactor 2 activity were consistently very similar. The protein in the S-300 pool expressed both Factor V and APC-cofactor 2 activities, and manifested characteristics previously reported for Factor V (J. Clin. Invest. 66 583–591(1980)). Additional efforts to separate the two activities using several other chromatographic principles, such as Heparin Sepharose, Blue Sepharose and Wheat germ agglutinin Sepharose were unsuccessful (not shown), and APC-cofactor 2 activity was in fact found to purify together with Factor V on every chromatographic support that was tried.

SDS-polyacrylamide gel electrophoresis of the protein in the S-300 pool yielded a 330 kDA band (corresponding to single chain Factor V) in addition to bands with molecular weights of approximately 220,000 and 130–150,000 (FIG. 2). These bands represented cleaved Factor V and, like the 330 kDa species, they reacted with a polyclonal antiserum against Factor V on Western blotting (FIG. 2). The 220 kDa band represented the C-terminal part of Factor V, including the 74 kDa light chain of Factor $V_a$ and the larger (150 kDa) of the two activation fragments, and was recognized by an antiserum against the light chain of bovine Factor Va (results not shown). The 130–150 kDa bands comprised the N-terminal part of Factor V (105 kDa heavy chain plus the smaller of the two activation fragments), and accordingly reacted with an antiserum against the bovine Factor Va heavy chain (results not shown). Additional bands of lower molecular weights, which did not react with polyclonal Factor V antiserum on Western blotting were sometimes seen, but when present, their elution profiles (as judged by SDS-PAGE) on the S-300 chromatography did not correlate with the activity of Factor V or with APC-cofactor 2 activity. Incubation of the purified protein with thrombin yielded fragments characteristic for thrombin-cleaved Factor V, and concomitantly the activity in the APC-cofactor 2 assay was lost, suggesting APC-cofactor 2 activity only to be expressed by Factor V and not by Factor $V_a$. On Agarose gel electrophoresis, the purified protein migrated as a single species to an inter-alpha position (FIG. 2), and both Factor V and APC-cofactor 2 activities could be eluted from this position of the gel (not shown).

As Factor V is extremely sensitive to proteolysis, an abundance of protease inhibitors was included in the final protocol. When performed in the absence of protease inhibitors, the purification procedure resulted in a more degraded product lacking the 330 kDa species, but containing the 220 kDa and 130–150 kDa bands. This purified product expressed both Factor V and APC-cofactor 2 activities. Factor V requires calcium for its stability; and when calcium was not included in the purification, both Factor V and APC-cofactor 2 activities were gradually lost.

The protein in the S-300 pool was used as antigen, as described above, for the production of monoclonal antibodies. Seventeen antibodies were obtained, and they were all found to react with the 330 kDa single chain Factor V as well as with the 220 kDa species, as judged by Western blotting (FIG. 2). After thrombin cleavage of Factor V, all antibodies reacted with the 150 kDa activation fragment (the larger of the two activation fragments).

One of the antibodies (Master 30) was immobilized on Affigel and used for affinity chromatography (FIG. 3). The S-300 pool was applied to the column. The protein that bound to the column was eluted and found to have both Factor V and APC-cofactor 2 activities. The elution profiles of both activities coincided, but manifested considerable trailing. Other elution conditions such as using higher or lower pH, or denaturing agents were tried but were unsuccessful as they resulted in loss of both activities. The S-300 pool was also applied to columns with immobilized polyclonal antibodies against human Factor V or against bovine Factor $V_a$ fragments. Both Factor V and APC-cofactor 2 activities were retained on the columns, but the denaturing conditions required to elute the bound protein resulted in loss of both biological activities (results not shown).

Figure 4A:
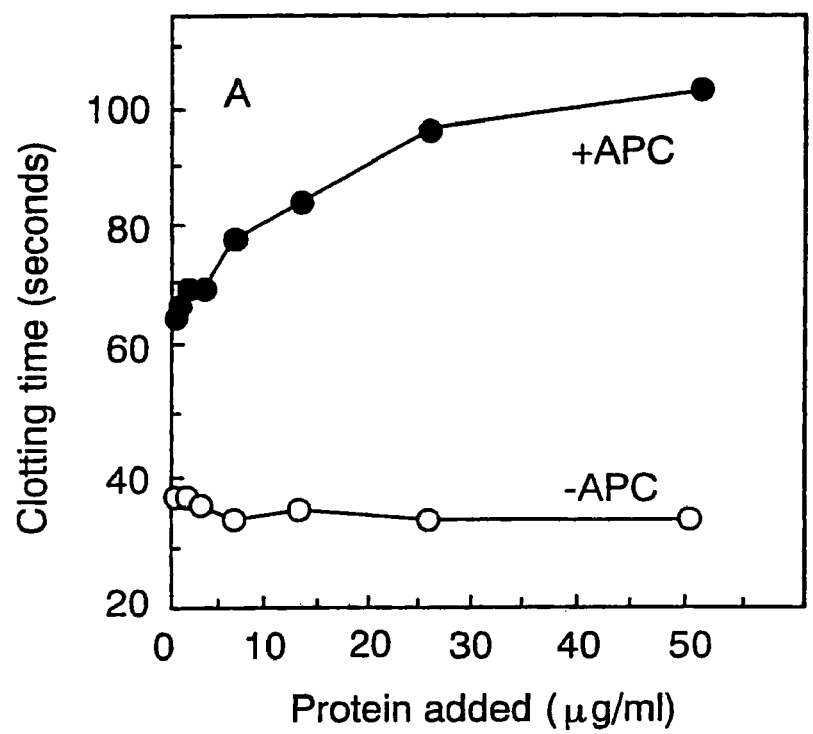
FIG. 4 illustrates correction of APC-resistance by purified APC-cofactor 2 activity/Factor V.
Figure 4B:
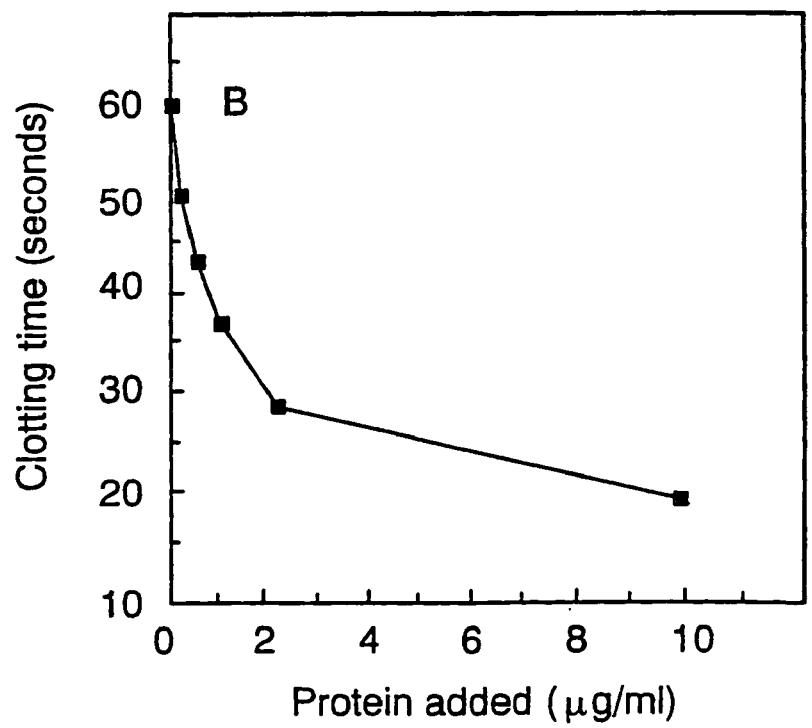
Figure 5:
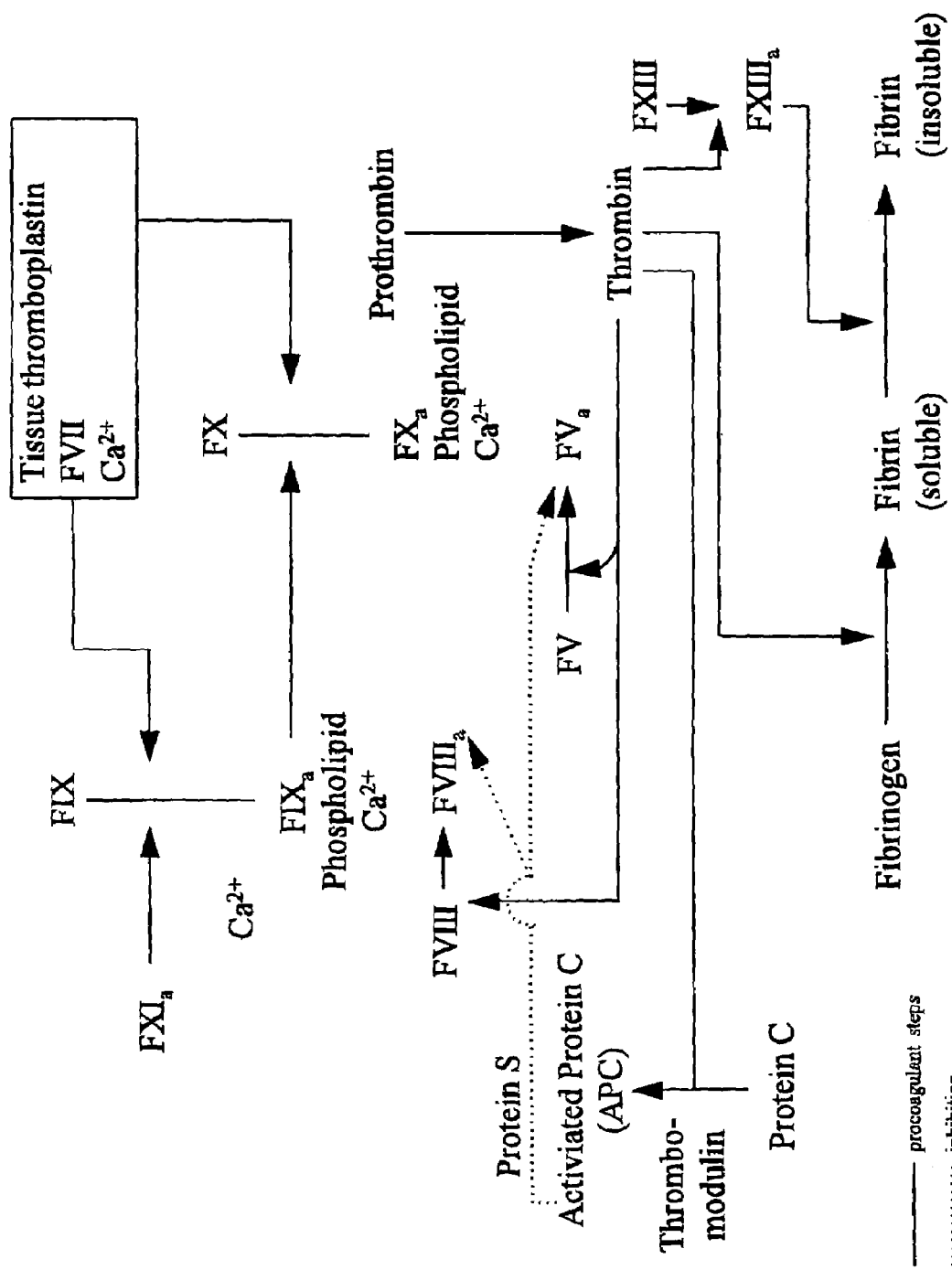
FIG. 5 illustrates the elements and interactions of the human blood coagulation system.

Increasing concentrations of affinity purified APC-cofactor 2/Factor V were added to AS plasma and the anticoagulant response to APC tested. A dose-dependent increase in anticoagulant response to APC was observed (FIG. 4A). Approximately 25 mg/L, which is of the same order of magnitude as the normal plasma concentration of Factor V, was required to yield an APC-response of AS plasma comparable to that of normal plasma (clotting times in the presence of APC of 90–110 seconds). The affinity purified protein was also active in Factor V assay, as demonstrated by a shortening of the clotting time (FIG. 4B).

Assays for Components in the APC-Cofactor System

The following examples show that by keeping the levels constant of two of the components in the APC-cofactor system comprised of APC, Factor V having APC-cofactor 2 activity and Protein S, and varying the remaining one, different substrate conversion rates will be achieved. This implies that assays as outlined above for each of the components can be constructed. An assay employing plasma deficient in APC-cofactor 2 activity has been disclosed above.

Effect of APC-Cofactor 2 in a Chromogenic Assay.

The assay principle is based upon the monitoring of the degradation of $FVIII_a$ by APC through the $FIX_a$-dependent activation of FX, in which system $FVIII_a$ serves as an important cofactor to $FIX_a$. Thus, a decreased level of $FVIII_a$ will result in a decreased generation of $FX_a$, determined through the hydrolysis of a $FX_a$-sensitive chromogenic peptide substrate.

I. 50 μL of a normal plasma dilution 1:20 in 50 mmol/L Tris-HCl buffer, pH 7.3, I=0.15 and 1% bovine serum albumin (BSA) containing highly purified FVIII concentrate (Octonativ M®, Kabi Pharmacia AB, Stockholm Sweden), 2 IU/mL, was mixed with 50 μL bovine thrombin, 0.06 nkat/mL (activity vs. the substrate S-2238, (Chromogenix AB, Mölndal, Sweden)) for 30 sat 37° C.

II. Thereafter 100 μL of a reagent (R) mixture containing 40 mmol/L Tris-HCl, pH 7.3 and 0.15% BSA, $CaCl_2$, 12 mmol/L, and phospholipids, 30 μmol/L, as well as other components defined below, was added to the above mixture, followed by an incubation for 2 min at 37° C.

III. 25 μL was then subsampled from this mixture and diluted with 1000 μL 50 mmol/L Tris-HCl buffer, pH 7.3, I=0.15 with 0.2% BSA, followed by analysis of FVIII activity according to the COATEST® FVIII assay principle (Chromogenix AB, Mölndal, Sweden).

IV. 200 μL of a reagent containing bovine $FIX_a$ and bovine FX (COATEST FVIII, Chromogenix AB, Mölndal, Sweden) and phospholipids, 30 μmol/L, was mixed with 100 μL of the diluted subsample and with 100 μL $CaCl_2$, 25 mmol/L. After 5 minutes incubation at 37° C., 200 μL of the chromogenic $FX_a$ substrate S-2765 (Chromogenix AB, Mölndal, Sweden), 0.9 mmol/L was added. After further 3 min incubation at 37° C., the substrate hydrolysis was stopped by addition of 100 μL acetic acid, 20%, and the absorbance of the released Chromophore pNA (p-nitroaniline) was read at 405 nm in a photometer.

In this assay system, the concentration of active FVIII in the sample is directly proportional to the absorbance. The content of supplementary components in the different R-mixtures are:

A. None
B. APC, 0.4 μg/mL
C. APC, 0.4 μg/mL+APC-cofactor 2 activity, 0.3 U/mL
D. APC, 0.4 μg/mL+human Protein S, 1 μg/mL
E. APC, 0.4 μg/mL+human Protein S, 1 μg/mL+APC-cofactor 2 activity, 0.3 U/mL Normal plasma contains approximately 10 μg/mL of free Protein S, hence the sample dilutions contributes with 0.05× 0.05×10=0.025 μg in stage II, corresponding to one fourth of the added amount of purified human Protein S. The content of APC-cofactor 2 activity should be considered as an approximate estimation since no quantitative method yet exists.

| R-Mixture | Protein S, conc. in stage II, μg/mL | A 405 | Effect of APC-Cofactor 2 activity on APC activity expressed as Δ405 |
|---|---|---|---|
| A | 0.125 | 0.678 | |
| B | 0.125 | 0.623 | |
| C | 0.125 | 0.509 | −0.114 (C−B) |

-continued

| R-Mixture | Protein S, conc. in stage II, µg/mL | A 405 | Effect of APC-Cofactor 2 activity on APC activity expressed as Δ405 |
|---|---|---|---|
| D | 0.625 | 0.559 | |
| E | 0.625 | 0.389 | −0.170 (E–D) |

Thus, the results show that addition of APC-cofactor 2 activity enhances the activity of APC at both levels of Protein S, illustrated as a decrease in the $FX_a$-generation, i.e., an increased rate of inactivation of $FVIII_a$ in stage II.

Effect of APC-Cofactor 2 Activity in Clotting Assay.

Cofactors $FV_a$ and $FVIII_a$ are involved in the generation of thrombin, the enzyme responsible for fibrin formation. These cofactors are degraded by APC and hence the activity of APC is illustrated in a clotting assay as a prolongation of the time needed for generation of the fibrin clot. Since Protein C(PC) circulates as a proenzyme, activation of PC in the sample is accomplished by addition of the snake venom enzyme Protac C® (Pentapharm, Basel, Switzerland). The following experiment was performed:

I. 10 µL FVIII concentrate (Octonativ M®, Kabi Pharmacia AB, Stockholm, Sweden), 10 IU/mL, was mixed with 100 µL PC-deficient plasma, 100 µL APTT reagent, 25 µL Protac C®, 1.5 U/mL, and 25 µL of a reagent (R) mixture containing 50 mmol/L Tris-HCl, pH 7.5, I=0.15, 0.2% BSA and further components defined below, was added to the above mixture. The complete mixture was incubated for 4 min at 37° C.

II. 100 µL $CaCl_2$, 22 mmol/L, was then added to the above mixture and the time needed for clot formation at 37° C. was recorded.

Supplementation in R-mixtures:
A. None
B. PC, 2 µg/mL
C. PC, 2 µg/mL, +APC-cofactor 2 activity, 2.6 U/mL
D. PC, 4 µg/mL
E. PC, 4 µg/mL, +APC-cofactor 2 activity, 2.6 U/mL
F. APC-cofactor 2, 2.6 U/mL The Protein C deficient plasma contributes the other plasma proteins involved in the clotting process as well as Protein S, a cofactor for APC. The final concentration of APC-cofactor 2 activity in stage I is approximately 0.2–0.3 U/mL (see above).

| R-Mixture | Concentration of PC in stage I, µg/mL | Clotting time, s | Prolongation of APC activity due to APC-Cofactor 2, s Δ |
|---|---|---|---|
| A | 0 | 42.3 ± 0.7 (n = 5) | |
| B | 0.2 | 62.7 ± 1.2 (n = 5) | |
| C | 0.2 | 71.4 ± 1.6 (n = 3) | 8.7 |
| D | 0.4 | 79.3 ± 2.9 (n = 5) | |
| E | 0.4 | 104.5 ± 8.6 (n = 3) | 25.2 |
| F | 0 | 45.9 | |

Thus, the experiments clearly show that addition of APC-cofactor 2 activity enhances the APC activity, expressed as an increased prolongation of the clotting time. The effect of the addition of the APC-cofactor 2 preparation in the absence of PC is only minor.

The invention claimed is:

1. A method for determining, in a sample derived from a human, a functional activity of anticoagulant Factor V of the human blood coagulation system, which activity can be correlated to conversion of a substrate specific for activated Protein C (APC), said method comprising
measuring in an assay medium containing said sample and a substrate for APC, conversion of said substrate by APC and correlating said conversion to said functional activity of said anticoagulant Factor V;
wherein said assay medium includes a plasma preparation which is deficient in anticoagulant Factor V activity; and
wherein exogenous APC is added to said assay medium.

2. A method as in claim 1, wherein said substrate for APC is selected from the group consisting of Factor Va and Factor VIIIa.

3. A method as in claim 2, wherein the sample is derived from an individual on therapy with vitamin K antagonists or otherwise deficient in vitamin K-dependent coagulation factors, and wherein at least one vitamin K dependent coagulation factor in activated or inactivated form is added to the assay medium.

4. A method as in claim 1, wherein said plasma preparation comprises human plasma which has been made deficient in said anticoagulant Factor V activity.

5. A method as in claim 1, wherein said sample comprises human plasma from individuals deficient in said anticoagulant Factor V activity and wherein said sample has an anticoagulant Factor V activity at a level detectably below the level in normal human plasma.

6. A method as in claim 1, wherein said method further comprises adding to the assay medium a blood coagulation factor or a reagent that activates the blood coagulation system via a pathway selected from the group consisting of the intrinsic and extrinsic pathways.

7. A method as in claim 1, wherein said method further comprises adding blood coagulation components selected from the group consisting of Factor VII/VIIa, Factor IX, Factor IXa, Factor X/Xa, Factor II, Factor XIa, Factor XIIa and a reagent that serves to introduce an activated coagulation factor.

8. A method as in claim 7, wherein said reagent that serves to introduce an activated coagulation factor is selected from the group consisting of a contact activator and a tissue factor.

9. A method as in claim 1, wherein said plasma preparation which is deficient in anticoagulant Factor V activity is selected from the group consisting of human plasma which has been made deficient in said anticoagulant activity, and human plasma from one or more individuals deficient in said anticoagulant activity.

10. A method as in claim 1, further comprising a comparison of multiple samples and wherein the functional activity of said exogenous APC added to each sample is essentially constant between said samples.

11. A method as in claim 10, wherein a functional excess of said exogenous APC is added to each sample to achieve said essentially constant functional activity.

12. A method as in claim 10, wherein an antibody which specifically binds to an epitope associated with anticoagulant activity of Protein S is added to each sample to achieve said essentially constant functional activity.

13. A method as in claim 1, further comprising adding to said assay medium a substance selected from the group consisting of Factor VIII and VIIIa.

14. A method as in claim 1, wherein said sample is a blood or blood derived sample.

15. A method as in claim 1, wherein said determination of said functional activity is used to diagnose a blood coagulation disorder in an individual from which said sample is derived.

16. A method for diagnosing a blood coagulation/anticoagulation disorder or for determining a predisposition thereto in a human, said method comprising
   determining anticoagulant Factor V activity in an assay medium containing a sample derived from said human,
   wherein said assay medium further comprises a plasma preparation which is deficient in anticoagulant Factor V, and
   wherein an abnormal level indicates manifestation of, or predisposition to, said disorder.

17. A method as in claim 16, wherein said disorder is a thromboembolic disorder.

18. A method as in claim 17, wherein said abnormal level is a decreased level.

19. A method as in claim 16, wherein said anticoagulant Factor V activity can be correlated to conversion of a substrate specific for activated Protein C (APC), said method further comprising:
   measuring in said assay medium, containing said sample and a substrate for APC, conversion of said substrate by APC and correlating said conversion to said anticoagulant Factor V activity;
   wherein at least one exogenous substance selected from the group consisting of Protein S and an inhibitor of Protein S activity is added to said assay medium.

20. A method as in claim 16, wherein the method further comprises adding to the assay medium a blood coagulation factor or a reagent that activates the blood coagulation system via a pathway selected from the intrinsic and extrinsic pathways.

21. A method as in claim 16, said method further comprising adding blood coagulation components selected from the group consisting of Factor VII/VIIa, Factor IX, Factor IXa, Factor X/Xa, Factor II, Factor XIa Factor XIIIa and a reagent that serves to introduce an activated coagulation factor.

22. A method as in claim 21, wherein said reagent that serves to introduce an activated coagulation factor is selected from the group consisting of a contact activator and a tissue factor.

23. A method as in claim 16, wherein said sample comprises human plasma from individuals deficient in said anticoagulant Factor V activity and wherein said sample has an anticoagulant Factor V activity at a level detectably below the level in normal human plasma.

* * * * *

UNITED STATES PATENT AND TRADEMARK OFFICE
CERTIFICATE OF CORRECTION

PATENT NO. : 7,169,572 B1  Page 1 of 1
APPLICATION NO. : 08/500917
DATED : January 30, 2007
INVENTOR(S) : Dahlbäck It is certified that error appears in the above-identified patent and that said Letters Patent is hereby corrected as shown below:

On the Title Page, item 56 under the heading References Cited, U.S. Patent Documents, add:
-- 5,705,395 * 1/1998 Griffin et al.
   5,726,028 * 3/1998 Kraus
   5,753,510 * 5/1998 Kraus
   5,766,869 * 6/1998 Arkel et al. --.

On the Title Page, item 56 under the heading References Cited, Other Publications, add:
-- Blombäck, M. et al. (1987), "Chromogenic Peptide Substrates in the Laboratory Diagnosis of Clotting Disorders," *Haemostasis and Thrombosis*, Bloom and Thomas (eds.), 2$^{nd}$ ed, 967-981.
Cornillon, B. et al. (1986), "Rat Coagulation Factor V Purification and Production of the Monospecific Antiserum," *Comp. Biochem. Physiol.*, Vol. 83B, 2:397-401.
Cripe, L.D. et al. (1992), "Structure of the Gene for Human Coagulation Factor V," *Biochemistry*, 31:3777-3785.
Kamiya, T. et al. (1986), "Inherited Deficiency of Protein S in a Japanese Family with Recurrent Venous Thrombosis: A Study of Three Generations," *Blood*, 67(2):406-410.
Kobayashi, I. et al. (1989), "Functional Activity of Protein S Determined with Use of Protein C Activated by Venom Activator," *Clin. Chem.*, 35(8):1644-1648.
Martinoli, J.L. et al. (1986), "Fast Functional Protein C Assay Using Protac, A Novel Protein C Activator," *Thrombosis Research*, 43:253-264.
McAlphine, P.J. et al. (1990), "A *Pst*I Polymorphism in the Human Coagulation Factor V (F5) Gene," *Nucleic Acids Research*, 18(24):7471.
Nilsson, I.M. (1987), "Assessment of Blood Coagulation and General Haemostasis," *Haemostasis and Thrombosis*, Bloom and Thomas (eds.), 2$^{nd}$ ed, 922-932.
Voet, D. et al. (eds.) (1990), "Biochemistry," John Wiley & Sons, Inc. 1086-1095. --

Col. 24, line 4, add a -- , -- after the term "Factor XIa".
Col. 24, line 4, delete "Factor XIIIa" and replace it with -- Factor XIIa --.

Signed and Sealed this

Ninth Day of February, 2010

David J. Kappos
*Director of the United States Patent and Trademark Office*